United States Patent
Liu et al.

(10) Patent No.: US 9,340,562 B1
(45) Date of Patent: May 17, 2016

(54) CHROMATOGRAPHIC MATERIAL AND METHOD FOR PREPARATION THEREOF

(71) Applicants: DIONEX CORPORATION, Sunnyvale, CA (US); THERMO ELECTRON MANUFACTURING LIMITED, Runcorn (GB)

(72) Inventors: Xiaodong Liu, Cupertino, CA (US); Richard T. Williams, Runcorn (GB); Xiao Cui, Sunnyvale, CA (US)

(73) Assignees: Thermo Electron Manufacturing Limited, Altrincham (GB); Dionex Corporation, Sunnyvale, CA (US)

( * ) Notice: Subject to any disclaimer, the term of this patent is extended or adjusted under 35 U.S.C. 154(b) by 0 days.

(21) Appl. No.: 14/526,996

(22) Filed: Oct. 29, 2014

(51) Int. Cl.
 C07F 7/04 (2006.01)
 G01N 30/02 (2006.01)
 C07F 7/08 (2006.01)
 C07B 63/00 (2006.01)

(52) U.S. Cl.
 CPC .............. *C07F 7/0856* (2013.01); *C07B 63/00* (2013.01); *C07F 7/0885* (2013.01)

(58) Field of Classification Search
 CPC .......... C07F 7/04; B01D 15/08; B01D 39/00; G01N 30/02
 USPC .................... 556/413; 210/656, 502.1, 198.2; 436/161
 See application file for complete search history.

(56) References Cited

U.S. PATENT DOCUMENTS

| | | | |
|---|---|---|---|
| 5,589,069 A * | 12/1996 | Wenzhi ................ | B01D 15/364 210/635 |
| 6,884,345 B1 | 4/2005 | Irgum et al. | |
| 7,402,243 B2 | 7/2008 | Liu et al. | |
| 2005/0023203 A1 | 2/2005 | Orlovsky et al. | |
| 2006/0054559 A1* | 3/2006 | Liu et al. ...................... | 210/656 |
| 2006/0169638 A1 | 8/2006 | Zelechonok et al. | |
| 2009/0202816 A1 | 8/2009 | Schlenoff | |
| 2010/0300971 A1* | 12/2010 | Jiang et al. .................... | 210/656 |

FOREIGN PATENT DOCUMENTS

| EP | 2210662 A2 | 7/2010 |
|---|---|---|
| EP | 2745903 A1 | 6/2014 |
| WO | 8908130 | 9/1989 |
| WO | 9111241 | 8/1991 |
| WO | 2006088760 A1 | 8/2006 |

OTHER PUBLICATIONS

By Qui et al., Analyst (Cambridge, U.K.) (2009), 134(3), 460-465 (Qui-1).*
Qui et al., Journal of Chromatography A (2007), 1163(1-2), 63-69 (Qui-2).*
Badea et al., "Simultaneous Determination of Some Analgesic Drugs Using Mixed Mode Stationary Phase," Chromatographia, 76, 1459-1465, 2013.
Brunetto et al., "High-performance liquid chromatographic determination of cocaine and benzoylecgonine by direct injection of human blood plasma sample into an alkyl-diol-silica (ADS) precolumn," Anal. Bioanal. Chem., 375, 534-538, 2003.
Calinescu et al., "HPLC Separation of Acetaminophen and its Impurites Using a Mixed-mode Reversed-Phase/Cation Exchange Stationary Phase," J. of Chromatographic Science, 50, 335-342, 2012.
Chromatography OnLine, Alltech Mixed-Mode Columns, 1 page, downloaded Jul. 29, 2015.
Cohen and Leonard, "Immobilized artificial membrane chromatography: a rapid and accurate HPLC method for predicting bile salt-membrane interactions," J. Lipid Research, vol. 36, 2251-2280, 1995.
DIONEX Datasheet, Acclaim Mixed-Mode WAX-1 Column, 8 pages, 2007.
DIONEX Datasheet, Acclaim Mixed-Mode WAX-1 LC Column, 2 pages, 2014.
DIONEX Datasheet, Acclaim Mixed-Mode WCX-1 for Separating Basic Molecules, 8 pages, 2008.
DIONEX Datasheet, Acclaim Trinity P1 Column, 6 pages, 2010.
Greco et al., "Serial coupling of reversed-phase and zwitterionic hydrophilic interaction LD/MS for the analysis of polar and nonpolar phenols in wine," J Sep Sci, vol. 36, 1379-1388, 2013.

(Continued)

*Primary Examiner* — Porfirio Nazario Gonzalez
*Assistant Examiner* — Kofi Adzamli
(74) *Attorney, Agent, or Firm* — Timothy J. Ohara

(57) ABSTRACT

A chromatographic material comprising a zwitterionic ligand covalently bound to a substrate, the ligand preferably has a formula II:

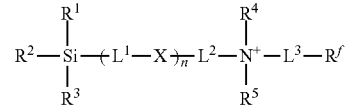

wherein
$R^1$, $R^2$, $R^3$ are independently selected from an oxygen atom that is configured to connect to a substrate atom in the substrate, an oxygen atom that is configured to connect to a silicon atom of an adjacent ligand, a hydroxyl group, a halogen atom, an alkoxy group, a dialkylamino group, an acyl group, an alkyl group, or an aryl group;
$L^1$, $L^2$ and $L^3$ are independently hydrophobic moieties; each containing 2 to 30 carbon atoms, wherein there are at least 10 carbon atoms in the combined chain lengths of $L^1$, $L^2$ and $L^3$;
X is an O atom, S atom, amide group or sulfonamide group;
n is 0 or 1;
$R^4$, $R^5$ are independently selected from a hydrogen atom or a hydrocarbon moiety containing 1 to 20 carbon atoms; and
$R_f$ is a negatively charged moiety comprising a sulfonic, carboxylic, or phosphonic functional group.

20 Claims, 12 Drawing Sheets

(56) References Cited

OTHER PUBLICATIONS

Lantz et al., "Simultaneous Resolution and Detection of a Drug Substance, Impurities, and Counter Ion Using a Mixed-Mode HPLC Column with Evaporative Light Scattering Detection," J. Liq. Chrom. & Rel. Technol., 20(9), 1409-1422, 1997.

Liu et al., "Chromatographic evaluation of reversed-phase/anion-exchange-cation-exchange trimodal stationary phases prepared by electrostatically driven self-assembly process," J of Chromatography, 1218(22), 3407-3412, 2011.

Liu et al., "HILIC Behavior of a Reversed-Phase/Cation Exchange/Anion Exchange Trimode Column," Journal of Separation Science, vol. 33: 6-7, 779-786, 2010.

Nesterenko et al., "Zwitterionic ion-exchangers in ion chromatography: A review of recent developments," Analytica Chimica Acta, 652. 3-21. 2009.

SILEC Technologies Datasheet, Obelisc, LC Columns with Liquid Separation Cell Technology, 6 pages.

SILEC Technologies Datasheet, Primesep HPLC Columns, 1 page, 2002-2014.

Yu and Hartwick, "Zwitterionic Stationary Phases in HPLC," J. of Chromatographic Science, vol. 27, 176-185, Apr. 1989.

Buszewski et al., "Hydrophilic interaction liquid chromatography (HILIC)—a powerful separation technique," Anal. Bioanal. Chem. 402, 231-247, 2012.

* cited by examiner

CHROMATOGRAPHIC MATERIAL AND METHOD FOR PREPARATION THEREOF

FIELD

This invention relates to the field of chromatographic sample separation that includes liquid chromatography and solid phase extraction and, in particular, it relates to material and the synthesis of material for use as a stationary phase in chromatographic sample separation. The invention, in particular, relates to material for use as a mixed mode stationary phase. The invention further relates to chromatographic columns containing the stationary phase and applications thereof.

BACKGROUND

Liquid chromatography (LC), e.g. HPLC and UHPLC, and solid phase extraction (SPE) are used routinely in both analytical and preparative chromatography applications. In these chromatographic techniques, separation of a sample comprising a mixture of components (also termed analytes) is achieved by conveying the sample in a liquid mobile phase through a stationary phase in a column, thereby causing the sample to separate into its components due to different partitioning between the mobile and stationary phases of each of the components (i.e. the components have different partition coefficients). The stationary phase is typically in the form of a bed of particles packed within the column, or in the form of a monolithic material held in the column.

A bed of non-porous particles has a relatively low sample capacity. Therefore, porous particles are commonly used which contain a network of pores to increase the surface area of the stationary phase and thus improve the capacity of the separation. The porous particles may be fully porous, wherein the pores extend throughout the bulk of the particles. As an alternative to fully porous particles, more recently use has been made of so-called fused core particles, which are also termed superficially porous particles. These are particles that have a non-porous core (also termed a fused or solid core) and are porous only in an outer layer or region that surrounds the non-porous core. Silica particles are commonly used as the stationary phase, either as non-porous, fully porous or superficially porous particles.

The selectivity of a stationary phase for analytes is mainly governed by column chemistry, which is key in LC separation. Although reversed-phase (RP) columns (e.g. columns comprising a C18 stationary phase) are most commonly used in pharmaceutical applications, they often fail to retain highly polar molecules (e.g. counter ions) and offer limited selectivities. Instead, ion exchange (IEX) chromatography is typically used to separate ionic or ionizable molecules. However, IEX has limited use in organic molecule separations due to inadequate hydrophobic retention. Ion Pairing chromatography can help to alleviate the aforementioned difficulties by allowing ionic analytes to be separated on a reversed-phase column but it has drawbacks in that it often requires extended equilibration time, a complicated mobile phase with high salt content that is incompatible with mass spectrometry (MS), and a dedicated column.

Mixed-mode chromatography provides a viable solution to the aforementioned challenges by utilizing a stationary phase that provides both reversed-phase and ion-exchange retention mechanisms. An advantage of the mixed-mode approach is that column selectivity can easily be modified by adjusting mobile phase ionic strength, pH and/or organic solvent concentration. As a result, not only is the selectivity of a mixed-mode column complementary to that of reversed-phase columns, but it also allows for the development of multiple complementary selectivities on a given column under different appropriate conditions. Mixed-mode chromatography is well-suited to retaining ionic, hydrophobic (e.g. Naproxen), or hydrophilic (e.g. $Na^+$ and $Cl^-$ ions) analytes, and requires no ion-pairing agents, thereby significantly improving compatibility with MS. Many applications involving hydrophilic ionizable compounds that are problematic on a C18 column are easily addressed on a mixed-mode column. The use of the mixed-mode technique has been growing rapidly because of its advantages over conventional chromatography, such as its high resolution, adjustable selectivity, high sample loading, and its lack of need for ion-pairing agents.

Mixed-mode media can be classified into at least four categories based on column chemistry. The first type includes a blend of two different stationary phases (RP and IEX) (such as Thermo Scientific HYPERSIL™ Duet C18/SCX Mixed-mode Ion Exchange columns). The second type involves bonded silica modified by a mixture of both RP and IEX ligands in the bonding step (such as ALLTECH™ Mixed-Mode Columns). EP 2745903 A1 (Dionex) discloses the use of two or more different chromatographic moieties bound to a solid support, which have anion-exchange capabilities, cation-exchange capabilities, reverse-phase capabilities, or hydrophilic interaction capabilities. Although these first two types of media are relatively straightforward to synthesize, their use in many applications is limited by selectivity drifting, mainly due to the difference in hydrolytic stability between the RP and IEX ligand bonded sites.

The third and fourth types of mixed-mode media are more recent and use functional silyl ligands that contain both RP and IEX functionalities to covalently attach to silica particles. While the constant ratio between RP and IEX bonded sites greatly improves the selectivity robustness in these materials, a pronounced distinction exists between the third and fourth types. The third type of material uses IEX-embedded alkyl silyl ligands to modify the silica and can be viewed as an IEX-modified RP packing (such as PRIMESEP™ and OBELISC™ columns from SIELC Technologies). Further disclosure is contained in US 2005-0023203 A and in US 2006-0169638 A. By comparison, the fourth type material uses IEX-tipped silane ligand to functionalize the silica substrate, (such as disclosed in U.S. Pat. No. 7,402,243 and embodied in ACCLAIM™ Mixed-Mode columns from Thermo Fisher Scientific).

A technique that utilises a hydrophobic chain in combination with a zwitterionic end group is known as Immobilized Artificial Membrane Chromatography (IAMC). WO 89/08130, WO 91/11241 and D. E. Cohen and M. R. Leonard, *Journal of Lipid Research, Volume* 36, 1995, p. 2251-2260 describe this application and associated chemical structures. Specifically the hydrophobic chain and zwitterionic portion aims to mimic a biological membrane and is designed for the separation of biomolecules.

US 2010/0300971 A discloses phosphorylcholine-type zwitterionic moieties in the absence of a reversed phase component that are bound to a solid support for hydrophilic interaction liquid chromatography (HILIC). A maximum distance between the negative charge and the solid support of 10 atoms is specified.

In Greco et al, *J. Sep. Sci.*, 2013, 36, 8, 1379-1388, a technique is described wherein a reversed phase column is coupled with a zwitterionic phase column in series, with the obviously drawback of requiring two separate columns.

In L. W. Yu et al, *Zwitterionic Stationary Phases in HPLC, Journal of Chromatographic Science, Vol.* 27, April 1989, p. 176-185 is disclosed zwitterionic ligands, wherein relatively short ethyl or phenyl spacers are used as the linking group to the substrate, which limits their usefulness for reverse-phase chromatography.

In another approach, known as dynamically coating, a RP silica has been mixed with, for example, a zwitterionic surfactant having a hydrophobic tail group. The hydrophobic tail of the surfactant and the hydrophobic group bound to the silica associate together and form a co-mixture. Since the two components are not covalently attached to one another there is high potential to lose the zwitterionic surfactant from the system, thereby changing the chromatographic characteristics. A discussion of such phases and a general overview of zwitterionic phases can be found in E. P. Nesterenko et al, *Analytica Chimica Acta* 652 (2009) 3-21.

A recently developed class of mixed-mode separation media has been prepared by coating a porous solid support possessing a hydrophilic charged surface with polymer latex particles having the opposite charge via electrostatic attraction (see Journal of Chromatography A, 1218 (2011) 3407-3412 and ACCLAIM™ Trinity columns from Thermo Fisher Scientific). Due to the size of the latex particles (>50 nm) being larger than the size of the pores of the porous solid support (<30 nm), the outer surface of the support is functionalized by charged latex particles while the inner-pore area is intact and remains its original functionality and properties. Thus, the size-exclusion effect provides effective spatial separation between the inner-pore area and the outer surface so that the resulting material provides cation-exchange and anion-exchange properties at the same time. In addition, when the porous solid support is modified with hydrophilic interaction liquid chromatography (HILIC) and ion-exchange mixed-mode functionalities, after coating with the charged latex particles, the resulting material provides hydrophilic interaction liquid chromatography (HILIC), cation-exchange and anion-exchange functionalities (X. Liu and C. A. Pohl, *J. Sep. Sci.* 2010, 33, 779-786).

SUMMARY

According to an aspect of the invention there is provided a zwitterionic ligand for covalently bonding to a substrate, preferably for use in chromatographic material, wherein the ligand has a general formula I:

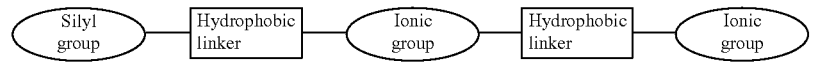

wherein the ionic groups have opposite charges to each other, there are at least 10 carbon atoms in the combined chain lengths of the hydrophobic linkers and the ligand is for bonding to the substrate through the silyl group.

According to another aspect of the invention there is provided a chromatographic material comprising the zwitterionic ligand covalently bound to a substrate, wherein the ligand is bound to the substrate through the silyl group. The chromatographic material is useful as a stationary phase in LC or SPE separations.

In a preferred embodiment the ligand has a formula II:

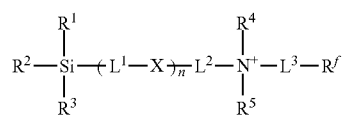

wherein
$R^1$, $R^2$, $R^3$ are independently selected from a hydroxyl group, a halogen atom, an alkoxy group, a dialkylamino group, an acyl group, an alkyl group, a heteroalkyl group, an aryl group, a heteroaryl group or a heterocycloalkyl group;

$L^1$, $L^2$ and $L^3$ are independently hydrophobic moieties; each containing 2 to 30 carbon atoms, wherein there are at least 10 carbon atoms in the combined chain lengths of $L^1$, $L^2$ and $L^3$;
X is an O atom, S atom, amide group or sulfonamide group;
n is 0 or 1;
$R^4$, $R^5$ are independently selected from a hydrogen atom or a hydrocarbon moiety containing 1 to 20 carbon atoms; and
$R_f$ is a negatively charged ionic moiety comprising a sulfonic, carboxylic, or phosphonic functional group. $R_f$ may be a negatively charged moiety selected from the group consisting of a sulfonic, carboxylic, and phosphonic functional group.

The bound ligand material thus may be represented by the general formula:

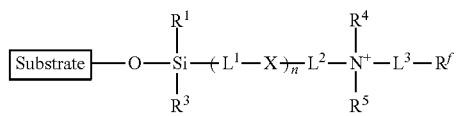

and, for example, with a silica substrate by the formula:

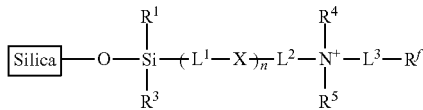

In the bound ligand, the $R^2$ group is an oxygen atom that is configured to connect to an atom in the substrate. In the bound ligand, $R^1$ and $R^3$, in addition to the mentioned groups, independently may be an oxygen atom that is configured to connect to an atom (e.g. an adjacent substrate atom) in the substrate or an oxygen atom that is configured to connect to a silicon atom of an adjacent ligand. For example, where the substrate is a silica substrate, at least one of the $R^1$ and $R^3$ groups may be an oxygen atom that is configured to connect to a silicon atom (e.g. an adjacent silicon atom) in the silica substrate.

The ligand of the invention bound to a suitable substrate provides a composition that is a zwitterionic/reversed-phase mixed-mode chromatographic material. It comprises a covalently bonded organic layer containing both hydrophobic interaction and zwitterionic functionalities. The hydrophobic linkers provide a reversed phase chromatographic functionality while the zwitterionic charged groups provide an ionic interaction chromatographic functionality. The preferred chemistry of chromatographic separation using the material is reversed phase, with ionic interaction capability (e.g. anionic interaction capability). The material can also provide separation of analytes based on hydrophilic interaction (HILIC). Thus, in embodiments, the material may provide reverse phase, HILIC and ion-interaction (e.g. anion-interaction) properties. The separation modes are typically dependent on the mobile phase composition. The separation modes may be selected or controlled by selecting or adjusting the mobile phase composition.

Unlike other mixed-mode material or stationary phases, the invention provides a class of separation material that provides reversed-phase (RP) retention moiety and a zwitterionic moiety with an overall net charge of zero or close to zero (substantially zero). In the case of some embodiments, depending on the pH of the mobile phase in a chromatographic separation, the material may behave as RP material, RP with a slight anion-interaction mixed-mode material, or RP with a slight cation-interaction mixed-mode material, or as HILIC material. This is the case, for example, when the following conditions are true: 1.) at least one of the ionic groups is a secondary amine, a tertiary amine, a carboxylic group or a phosphonic group, in other words, a pH dependent group; and 2.) the substrate is stable in a broad pH range say 1 to 12, so that the overall charge state can be practically modulated by pH. The material has numerous benefits, such as unique selectivity for a broad range of applications, flexible chemistry such that depending on specific applications the surface chemistry can be tailored accordingly. The material has the capability to separate both hydrophobic and ionic analytes. Furthermore, the material does not require the extended equilibration time and complicated mobile phase that is needed for ion pairing chromatography. The use of the zwitterionic moiety with an overall net charge of zero means that a lower salt content can be used in the mobile phase.

BRIEF DESCRIPTION OF THE DRAWINGS

FIG. 9 shows the hydrophobicity property of Phase 23a.
FIG. 10 shows the anion-exchange property of Phase 23a.
FIG. 11 shows the HILIC property of Phase 23a.
FIG. 12 shows the effect of solvent composition on the retention properties of Phase 23a.

DETAILED DESCRIPTION

Figure 1:
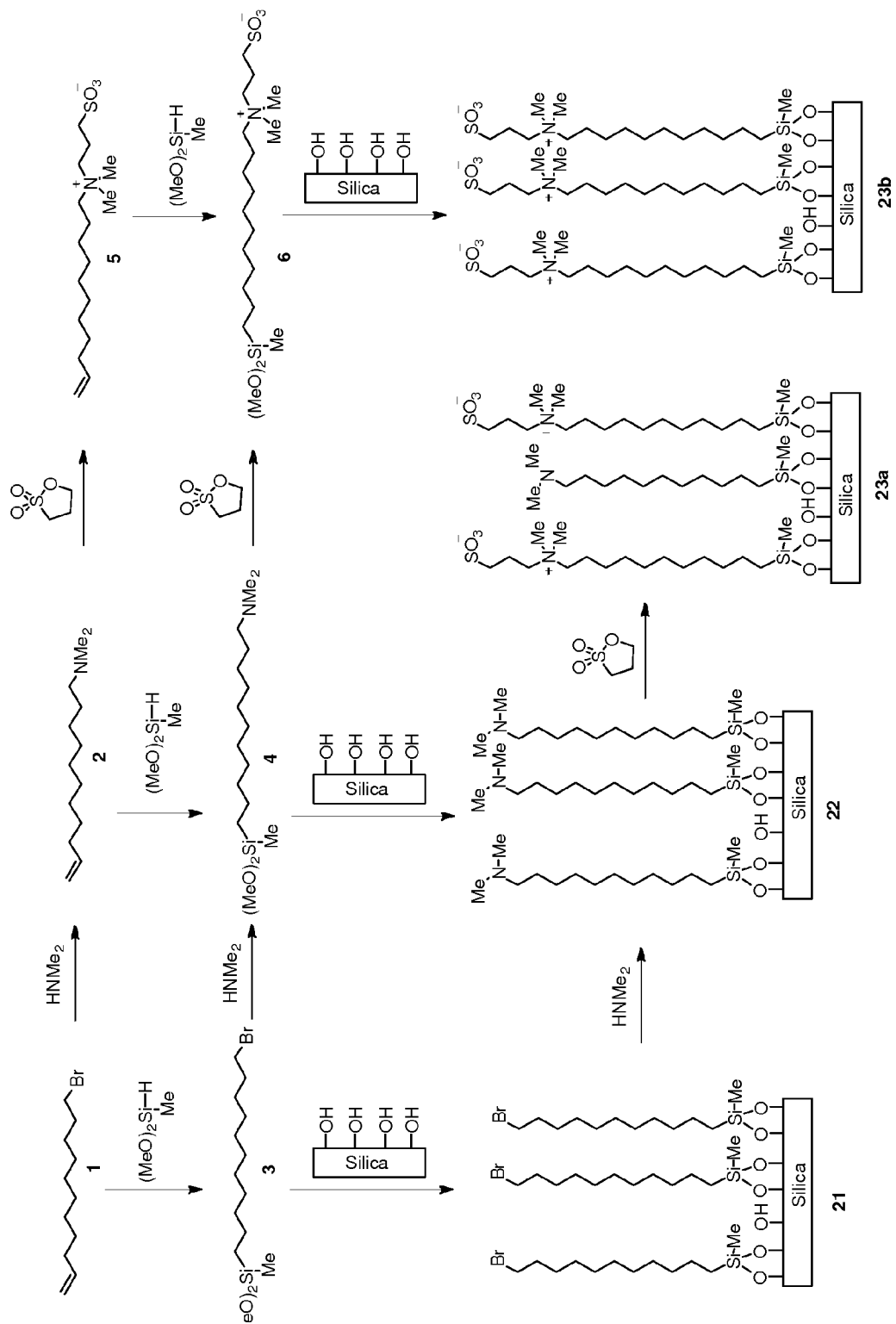
FIG. 1 shows a first set of embodiments of routes to preparing materials of the present invention.

Various preferred features, embodiments and examples of the invention will now be described in more detail.

DEFINITIONS

Herein the term "zwitterionic" ligand refers to a molecule that contains both positive and negative charges and carries a zero or substantially zero net charge.
Herein the term "hydrocarbon" and the like (e.g. hydrocarbon moiety) includes alkyl and aryl groups as herein defined. Herein, the term hydrophobic moieties and the like (e.g. hydrophobic linkers etc) includes alkyl and aryl groups as herein defined.
Herein the term "chain length", in relation to the hydrophobic linkers and their respective specific embodiments (e.g. $L^1+L^2$, and $L^3$), means the shortest chain length, in the first case (e.g. $L^1+L^2$) between the silicon atom of the silyl group and the central charged group (e.g. positively charged nitrogen atom) and in the second case (e.g. $L^3$) between the central charged group (e.g. positively charged nitrogen atom) and the end charged group (e.g. positively charged group). The combined chain lengths of the hydrophobic linkers, means the total, i.e. sum, of the chain lengths of the hydrophobic linkers.

Thus, in the case of straight chains, the chain lengths are numbered simply as, for example:

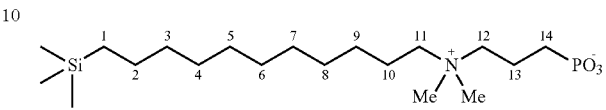

Chain branches are not included in the chain length count, as, for example:

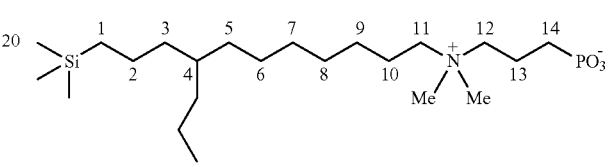

In the case of an aryl group, the number of carbon atoms in the shortest chain are counted, such that in a benzene ring the chain length counts as 4 for a para-linkage and 3 for a meta-linkage, for example:

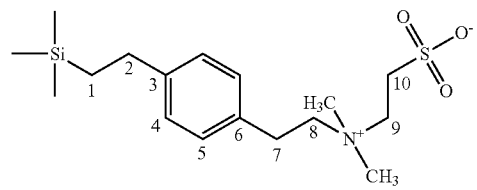 [SMILES: C[N+](C)(CCc1ccc(CC[Si](C)(C)C)cc1)CCS(=O)(=O)[O-]]

Any heteroatoms are not counted as carbon atoms in the chain length.

Herein the term "alkyl," by itself or as part of another substituent, means, unless otherwise stated, a straight or branched chain, or cyclic hydrocarbon radical, or combination thereof, which may be fully saturated, mono- or polyunsaturated and can include di- and multivalent radicals, having the number of carbon atoms designated (i.e., $C_1$-$C_{10}$ means one to ten carbons). Examples of saturated hydrocarbon radicals include, but are not limited to, groups such as methyl, ethyl, n-propyl (e.g., —$CH_2$—$CH_2$—$CH_3$, —$CH_2$—$CH_2$—$CH_2$—), isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "alkyl," unless otherwise noted, is also meant to include those derivatives of alkyl defined in more detail below, such as "heteroalkyl". Alkyl groups that are limited to hydrocarbon groups are termed "homoalkyl". The term "alkyl" can also mean "alkylene" or "alkyldiyl" as well as alkylidene in those cases where the alkyl group is a divalent radical.

Typical alkyl groups include, but are not limited to: methyl; ethyls such as ethanyl, ethenyl, ethynyl; propyls such as propan-1-yl, propan-2-yl, cyclopropan-1-yl, prop-1-en-1-yl, prop-1-en-2-yl, prop-2-en-1-yl (allyl), cycloprop-1-en-1-yl; cycloprop-2-en-1-yl, prop-1-yn-1-yl, prop-2-yn-1-yl, etc.; butyls such as butan-1-yl, butan-2-yl, 2-methyl-propan-1-yl, 2-methyl-propan-2-yl, cyclobutan-1-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, but-1-yn-1-yl, but-1-yn-3-yl, but-3-yn-1-yl, etc.; and the like.

Herein the term "alkylene" or "alkyldiyl" by itself or as part of another substituent means a divalent radical derived from an alkyl group, as exemplified, but not limited, by —$CH_2CH_2CH_2$— (propylene or propane-1,3-diyl), and further includes those groups described below as "heteroalkylene". Typically, an alkyl (or alkylene) group will have from 1 to about 30 carbon atoms, preferably from 1 to about 25 carbon atoms, more preferably from 1 to about 20 carbon atoms, even more preferably from 1 to about 15 carbon atoms and most preferably from 1 to about 10 carbon atoms. A "lower alkyl", "lower alkylene" or "lower alkyldiyl" is a shorter chain alkyl, alkylene or alkyldiyl group, generally having about 10 or fewer carbon atoms, about 8 or fewer carbon atoms, about 6 or fewer carbon atoms or about 4 or fewer carbon atoms.

Herein the term "alkylidene" by itself or as part of another substituent means a divalent radical derived from an alkyl group, as exemplified, but not limited, by $CH_3CH_2CH_2$= (propylidene). Typically, an alkylidene group will have from 1 to about 30 carbon atoms, preferably from 1 to about 25 carbon atoms, more preferably from 1 to about 20 carbon atoms, even more preferably from 1 to about 15 carbon atoms and most preferably from 1 to about 10 carbon atoms. A "lower alkyl" or "lower alkylidene" is a shorter chain alkyl or alkylidene group, generally having about 10 or fewer carbon atoms, about 8 or fewer carbon atoms, about 6 or fewer carbon atoms or about 4 or fewer carbon atoms.

Herein the terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

Herein the term "heteroalkyl," by itself or in combination with another term, means, unless otherwise stated, a stable straight or branched chain, or cyclic hydrocarbon radical, or combinations thereof, comprising the stated number of carbon atoms and at least one heteroatom selected from the group consisting of O, N, Si, S and B, and wherein the nitrogen and sulfur atoms may optionally be oxidized and the nitrogen heteroatom may optionally be quaternized. The heteroatom(s) O, N, B, S and Si may be placed at any interior position of the heteroalkyl group or at the position at which the alkyl group is attached to the remainder of the molecule. Examples include, but are not limited to, —$CH_2$—$CH_2$—O—$CH_3$, —$CH_2$—$CH_2$—$NHCH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—$S(O)_2$—$CH_3$, —CH=CH—O—$CH_3$, —Si($CH_3$)$_3$, —$CH_2$—CH=N—$OCH_3$, and —CH=CH—N($CH_3$)—$CH_3$. Up to two heteroatoms may be consecutive, such as, for example, —$CH_2$—NH—$OCH_3$ and —$CH_2$—O—Si($CH_3$)$_3$. Similarly, the term "heteroalkylene" by itself or as part of another substituent means a divalent radical derived from heteroalkyl, as exemplified, but not limited by, —$CH_2$—$CH_2$—S—$CH_2$—$CH_2$— and —$CH_2$—S—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like). Optionally, for alkylene and heteroalkylene linking groups, no orientation of the linking group is implied by the direction in which the formula of the linking group is written. For example, the formula —$CO_2R'$— optionally represents both —C(O)OR' and —OC(O)R'.

Herein the terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

Herein the terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo($C_1$-$C_4$)alkyl" is meant to include, but not be limited to, trifluoromethyl, 2,2,2-trifluoroethyl, 4-chlorobutyl, 3-bromopropyl, and the like.

Herein the term "aryl" means, unless otherwise stated, a polyunsaturated, aromatic, substituent that can be a single ring or multiple rings (preferably from 1 to 3 rings), which are fused together or linked covalently. The term "heteroaryl" refers to aryl groups (or rings) that contain from one to four heteroatoms selected from N, O, S, Si and B, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below.

For brevity, herein the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Each of the above terms (e.g., "alkyl," "heteroalkyl," "aryl" and "heteroaryl") are meant to include both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) are generically referred to as "alkyl group substituents," and they can be one or more of a variety of groups selected from, but not limited to: substituted or unsubstituted aryl, substituted or unsubstituted heteroaryl, substituted or unsubstituted heterocycloalkyl, —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —OS(O)$_2$R', —S(O)$_2$NR'R", —NRSO$_2$R", —CN and —NO$_2$ in a number ranging from zero to (2m'+1), where m' is the total number of carbon atoms in such radical. R', R", R'" and R"" each preferably independently refer to hydrogen, substituted or unsubstituted heteroalkyl, substituted or unsubstituted aryl, e.g., aryl substituted with 1-3 halogens, substituted or unsubstituted alkyl, alkoxy or thioalkoxy groups, or arylalkyl groups. When a compound of the invention includes more than one R group, for example, each of the R groups is independently selected as are each R', R", R'" and R"" groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are generically referred to as "aryl group substituents". The substituents are selected from, for example: substituted or unsubstituted alkyl, substituted or unsubstituted aryl, substituted or unsubstituted heteroaryl, substituted or unsubstituted heterocycloalkyl, —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R',—NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —CN and —NO$_2$, —R', —N$_3$, —CH(Ph)$_2$, fluoro(C$_1$-C$_4$)alkoxy, and fluoro(C$_1$-C$_4$)alkyl, in a number ranging from zero to the total number of open valences on the aromatic ring system; and where R', R", R'" and R"" are preferably independently selected from hydrogen, substituted or unsubstituted alkyl, substituted or unsubstituted heteroalkyl, substituted or unsubstituted aryl and substituted or unsubstituted heteroaryl. When a compound of the invention includes more than one R group, for example, each of the R groups is independently selected as are each R', R", R'" and R"" groups when more than one of these groups is present.

The zwitterionic ligand enables oppositely charged ionic groups to be attached to the surface, i.e. fixed in close proximity to the surface, of a substrate which thereby imparts unique phase selectivity towards small ions compared to standard mono-selective ion-exchange materials. The ligands are attached at the outer surface or within the volume of the stationary phase, i.e. on the surface within the pores of a porous substrate.

The ligand utilises a silyl group for attaching the ligand to the substrate (preferably silica substrate). The silyl group accordingly is preferably an activated silyl group, i.e. having groups (leaving groups) that can react with a substrate surface and enable attachment of the ligand to the substrate surface.

The silyl group preferably has a formula:

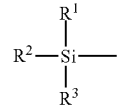

wherein $R^1$, $R^2$, $R^3$ are independently selected from an oxygen atom that connects to a substrate atom in the substrate or an oxygen atom that connects to a silicon atom of an adjacent ligand, a hydroxyl group, a halogen atom, an alkoxy group, a dialkylamino group, an acyl group, an alkyl group (optionally a heteroalkyl group or a heterocycloalkyl group), and an aryl group (optionally a heteroaryl group). More preferably $R^1$, $R^2$, $R^3$ are independently selected from a hydroxyl group, a halogen atom, an alkoxy group (i.e. methoxyl, ethoxyl, etc), an acyl, substituted or unsubstituted alkyl, substituted or unsubstituted heteroalkyl, substituted or unsubstituted aryl, substituted or unsubstituted heteroaryl and substituted or unsubstituted heterocycloalkyl.

The groups $R^1$, $R^2$ and $R^3$ may be the same or all different. Preferably, at least one of $R^1$, $R^2$, $R^3$ groups is a leaving group. More, preferably, at least one of $R^1$, $R^2$, $R^3$ groups is an alkoxy group (preferably methoxy, ethoxy or propoxy, especially methoxy), a dialkylamino group, or a halogen atom.

Preferably, there are at least 11 carbon atoms, or at least 12 carbon atoms, or at least 13 carbon atoms, or at least 14 carbon atoms, or at least 15 carbon atoms in the combined chain lengths of the hydrophobic linkers. Preferably, the total sum of carbon atoms in the hydrophobic linkers is at least 12, or at least 13, or at least 14 or at least 15, or more.

Preferably, there are at least 11 carbon atoms, or at least 12 carbon atoms, or at least 13 carbon atoms, or at least 14 carbon atoms, or at least 15 carbon atoms in the combined chain lengths of $L^1$, $L^2$ and $L^3$. Preferably, the total sum of carbon atoms in $L^1$, $L^2$ and $L^3 \geq 12$, or $\geq 13$, or $\geq 14$, or $\geq 15$.

Preferably, the linkers, $L^1$, $L^2$ and $L^3$ are independently hydrophobic moieties selected from substituted or unsubstituted alkyl and substituted or unsubstituted aryl.

In general, preferably one hydrophobic linker is longer than the other. Preferably, one of $L^2$ and $L^3$ is longer than the other. The longest hydrophobic linker preferably comprises an alkyl group, more preferably a homoalkyl group (substituted or unsubstituted, unsubstituted being preferred), more preferably a straight chain homoalkyl group, especially having 8, or 9, or 10, or 11, or 12, or more carbon atoms in the chain (i.e. at least 8, or at least 9, or at least 10, or at least 11, or at least 12 carbon atoms). A preferred homoalkyl chain length is 8 to 12 carbon atoms. Where one of the hydrophobic linkers, e.g. one of $L^2$ and $L^3$, comprises one of the aforesaid homoalkyl groups having 8, or 9, or 10, or 11, or 12, or more carbon atoms (or 8 to 12 carbon atoms), the other preferably comprises a homoalkyl group having a chain length of 6 carbon atoms or less, more preferably of 4 carbon atoms or less.

Preferably, the hydrophobic linkers, e.g. $L^2$ and $L^3$, are each straight chain homoalkyl groups. Preferably, at least one of the hydrophobic linkers comprises a homoalkyl group having at least 8 (especially 8 to 12) carbon atoms in the chain.

Where present, $L^1$ is preferably an alkyl group, more preferably a homoalkyl group (substituted or unsubstituted, unsubstituted being preferred), more preferably a straight chain homoalkyl group, especially having 2, or 3, or 4 carbon atoms.

In one type of embodiment: preferably, $L^2$ is a longer hydrophobic moiety than $L^3$. Preferably, $L^2$ comprises more carbon atoms than $L^3$. Preferably, $L^2$ comprises at least 8, at least 9, at least 10, or at least 11, or at least 12 carbon atoms. Preferably, $L^3$ comprises at least 2, or at least 3 or at least 4 carbon atoms. Preferably, $L^2$ comprises an alkyl group, more preferably a homoalkyl group (substituted or unsubstituted, unsubstituted being preferred), more preferably a straight chain alkyl group, especially having 8, or 9, or 10, or 11, or 12, or more carbon atoms (most preferably 10, or 11, or 12, or more carbon atoms). Preferably $L^3$ comprises an alkyl group, more preferably a homoalkyl group (substituted or unsubstituted, unsubstituted being preferred), more preferably a straight chain homoalkyl group, especially having 2, or 3, or 4 carbon atoms.

In another type of embodiment: preferably, $L^3$ is a longer hydrophobic moiety than $L^2$. Preferably, $L^3$ comprises more carbon atoms than $L^2$. Preferably, $L^3$ comprises at least 8, at least 9, at least 10, or at least 11, or at least 12 carbon atoms. Preferably, $L^2$ comprises at least 2, or at least 3, or at least 4 carbon atoms. Preferably, $L^3$ comprises an alkyl group, more preferably a homoalkyl group (substituted or unsubstituted, unsubstituted being preferred), more preferably a straight chain homoalkyl group, especially having 8, or 9, or 10, or 11, or 12, or more carbon atoms. Preferably $L^2$ comprises an alkyl group, more preferably a homoalkyl group (substituted or unsubstituted, unsubstituted being preferred), more preferably a straight chain homoalkyl group, especially having 2, or 3, or 4 carbon atoms.

Preferably, the central ionic group (positioned between the linkers) is a positively charged ionic moiety. The central ionic group is the ionic group at a central portion of the ligand. The central portion being in between the two hydrophobic linkers. The central ionic group preferably comprises a positively charged amino group, i.e. an ammonium ionic group, positioned between the linkers. Preferably, when either or both $R^4$, $R^5$ on the ammonium group are independently a hydrocarbon moiety containing 1 to 20 carbon atoms, said hydrocarbon moiety is an alkyl group, especially an alkyl group having 1 to 4 carbon atoms, wherein homoalkyl groups are preferred over heteroalkyl groups. Most, preferably $R^4$, $R^5$ are hydrogen or methyl, especially methyl.

Preferably, the end ionic group is a negatively charged ionic moiety. The end ionic group is the ionic group at an end portion of the ligand. Preferably, the end group $R^f$ is a negatively charged ionic moiety comprising a sulfonic, carboxylic, or phosphonic functional group (sulfonate, carboxylate or phosphonate). The negatively charged moiety may also be selected from the group consisting of a sulfonate, a carboxylate, and a phosphonate functional group.

The central ionic group and end ionic group are preferably separated by a hydrophobic linker comprising at least 2, more preferably at least 3, carbon atoms. The central ionic group and end ionic group may be separated by a hydrophobic linker comprising at least 4 carbon atoms. In some embodiments, the central ionic group and end ionic group may be separated by larger chains, i.e. of between 8 and 12 carbons atoms.

The substrate may be a particulate or monolithic substrate. The substrate material may be a metal oxide (which term herein includes a metalloid oxide), or an inorganic-organic hybrid material. The substrate may be a silica ($SiO_2$), silica/organo hybrid, alumina ($Al_2O_3$), titania ($TiO_2$), or zirconia ($ZrO_2$) substrate. A silica (which herein includes a silica/organo hybrid) substrate is most preferred. The substrate may be a synthetic resin substrate.

The formula of the material incorporating a substrate can be represented as:

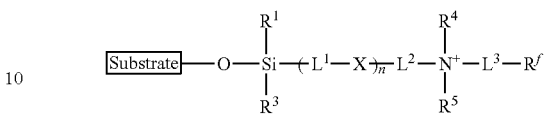

The formula of the material incorporating a silica substrate can be represented as:

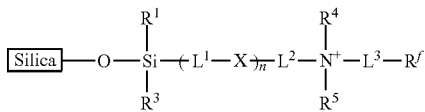

The substrate (preferably silica substrate) may be totally porous, superficially porous, or non-porous; and may be particulate or monolithic.

The substrate of the present invention is desirably a chromatographic material for use, for example, in LC or SPE applications.

The substrate is preferably particulate wherein particles of the substrate are typically and preferably substantially spherical but may be irregular in shape in some embodiments. The particles preferably have a narrow size distribution.

In certain examples, the particles are essentially "monodisperse" or essentially "homodisperse", which indicates that the particle size of the majority of the particles (e.g., 80, 90 or 95% of the particles) does not vary substantially (e.g., not more than 10%) below or above the median particle size ($D_{50}$). In an exemplary monodisperse particle population, 90% of the particles have an average particle size of between about $0.9 \times D_{50}$ and about $1.1 \times D_{50}$. This is advantageous for chromatographic applications. Whilst monodispersed particles are preferred, particles with a broader particle size distribution may be useful in many applications.

The particles are typically microparticles, preferably 0.1 μm or larger in median particle diameter, preferably up to 1000 μm in median particle diameter. More preferably the particles are from 1 to 1000 μm, or 0.1 to 500 μm or 1 to 500 μm in diameter, or still more preferably 0.1 to 100 μm or 1 to 100 μm in diameter, or even more preferably 0.2 to 50 μm in diameter, especially 0.1 to 10 μm or 1 to 10 μm and most preferably 1.5 to 5 μm in diameter.

The particles may be porous (including partially porous, totally porous or superficially porous) or non-porous particles. The particles may be useful for preparing solid core chromatographic materials.

When porous particles are formed, the pores of the particles can be of any size. The nominal pore size is typically measured in angstroms ($10^{-10}$ m, Å). A pore size distribution (PSD) is calculated from adsorption data using the BJH (Barrett Joyner-Halenda) method and the average pore size ($W_{BJH}$) is defined as the maximum of the PSD. In one example, the average size or diameter of the pores is between about 1 and about 5000 Å, especially between about 50 and about 5000 Å. In another example, the volume average diameter of the pores is between about 10 and about 5000 Å, between about 10 and about 4000 Å, between about 10 and about 3000 Å, between about 10 and about 2000 Å, between about 10 and about 1000 Å, between about 10 and about 800 Å, between about 10 and about 600 Å, between about 10 and about 500 Å, between about 10 and about 400 Å, between about 10 and about 300 Å, between about 10 and about 200 Å, between about 10 and about 100 Å, between about 20 and about 2000 Å, between about 20 and about 1000 Å, between about 20 and about 500 Å, between about 20 and about 300 Å, between about 20 and about 200 Å, between about 20 and about 100 Å, between about 30 and about 2000 Å, between about 30 and about 1000 Å, between about 30 and about 500 Å, between about 30 and about 300 Å, between about 30 and about 200 Å, between about 30 and about 100 Å, between about 40 and about 2000 Å, between about 40 and about 1000 Å, between about 40 and about 500 Å, between about 40 and about 300 Å, between about 40 and about 200 Å, between about 40 and about 100 Å, between about 50 and about 2000 Å, between about 50 and about 1000 Å, between about 50 and about 500 Å, between about 50 and about 300 Å, between about 50 and about 200 Å, between about 50 and about 100 Å, between about 60 and about 2000 Å, between about 60 and about 1000 Å, between about 60 and about 500 Å, between about 60 and about 300 Å, between about 60 and about 200 Å, between about 60 and about 100 Å, between about 70 and about 2000 Å, between about 70 and about 1000 Å, between about 70 and about 500 Å, between about 70 and about 300 Å, between about 70 and about 200 Å, between about 70 and about 100 Å, between about 80 and about 2000 Å, between about 800 $m^2/g$, between about 1 and about 600 $m^2/g$, between about 1 and about 500 $m^2/g$, between about 1 and about 400 $m^2/g$, between about 1 and about 200 $m^2/g$ or between about 1 and about 100 $m^2/g$. In another example, the specific surface area of the material is between about 10 and about 1,000 $m^2/g$, between about 10 and about 800 $m^2/g$, between about 10 and about 600 $m^2/g$, between about 10 and about 500 $m^2/g$, between about 10 and about 400 $m^2/g$, between about 10 and about 200 $m^2/g$ or between about 10 and about 100 $m^2/g$. In another example, the specific surface area of the material is between about 50 and about 1,000 $m^2/g$, between about 50 and about 800 $m^2/g$, between about 50 and about 600 $m^2/g$, between about 50 and about 500 $m^2/g$, between about 50 and about 400 $m^2/g$, between about 50 and about 200 $m^2/g$ or between about 50 and about 100 $m^2/g$. Preferably, the specific surface area of the particulate material is between about 1 and about 500 $m^2/g$, or between about 10 and about 500 $m^2/g$ (especially between about 50 and about 500 $m^2/g$). In another example, the specific surface area more preferably is between about 10 and about 100 $m^2/g$.

For non-porous particles, the specific surface area preferably is between about 0.5-10 $m^2/g$. For non-porous particles, the median particle diameter is preferably from 0.1 to 5 μm.

In view of the detailed description above, numerous preferred types of materials may be realised, as indicated in table 1 below:

TABLE 1

| Preferred embodiment | $R^1, R^2, R^3$ | n, $L^1$ | $L^2$ | $L^3$ | $R^4, R^5$ | $R_f$ |
|---|---|---|---|---|---|---|
| #1 | each independently methoxy, hydroxyl, or methyl, or O atom that connects to a substrate atom or silicon atom of an adjacent ligand | n = 0 | alkyl having a chain length of 8, or 9, or 10, or 11, or 12, or more carbon atoms, especially 8 to 12 carbon atoms, preferably straight chain, preferably unsubstituted | alkyl having a chain length of 2, or 3, or 4, or more carbon atoms, especially 2 to 4 carbon atoms, preferably straight chain, preferably unsubstituted | methyl | sulfonic, carboxylic, or phosphonic group |
| #2 | each independently methoxy, hydroxyl, or methyl, or O atom that connects to a substrate atom or silicon atom of an adjacent ligand | n = 0 | alkyl having a chain length comprising 2, or 3, or 4, or more carbon atoms, especially 2 to 4 carbon atoms, preferably straight chain, preferably unsubstituted | alkyl having a chain length of 8, or 9, or 10, or 11, or 12, or more carbon atoms, especially 8 to 12 carbon atoms, preferably straight chain, preferably unsubstituted | methyl | sulfonic, carboxylic, or phosphonic group |
| #3 | each independently methoxy, hydroxyl, or methyl, or O atom that connects to a substrate atom or silicon atom of an adjacent ligand | n = 0 | alkyl having a chain length of 8, or 9, or 10, or 11, or 12, or more carbon atoms, especially 8 to 12 carbon atoms, preferably straight chain, preferably unsubstituted | aryl, especially with a meta- or para-linkage having a chain length comprising respectively 3, or 4 carbon atoms, especially 4 carbon atoms, preferably unsubstituted | methyl | sulfonic, carboxylic, or phosphonic group | between about 80 and about 1000 Å, between about 80 and about 500 Å, between about 80 and about 300 Å, between about 80 and about 200 Å, between about 100 and about 200 Å, between about 100 and about 300 Å, between about 100 and about 400 Å, between about 100 and about 500 Å, between about 200 and about 500 Å or between about 200 and about 600 Å. Preferably, the average pore size is between about 30 and about 2000 Å, more preferably between about 80 and about 1000 Å. Most preferably, the average pore size is between about 80 and about 300 Å.

The (BET) specific surface area of the particulate substrate material is typically between about 0.1 and about 2,000 $m^2/g$, most typically between about 0.1 and about 1,000 $m^2/g$. For example, the specific surface area of the particulate material is between about 1 and about 1,000 $m^2/g$, between about 1 and The reverse-phase/zwitterionic mixed-mode ligands and materials of the invention may be synthesized by numerous advantageous synthetic routes as provided by a further aspect of the invention.

General Synthetic Procedure:

The materials, such as the materials according to any of the claims, can be synthesized by the following general methods:

General Method 1:

comprising:

1. covalently attaching a silyl ligand containing an alkyl or aryl moiety and an amino functional group to the substrate surface (by covalent bonding);
2. then allowing the amino functional group contained on the covalently attached silyl ligand to react with 1,3-propane sultone to form the chromatographic material.

General method 2:

comprising:

1. allowing a silyl ligand containing an alkyl or aryl moiety and an amino functional group to react with 1,3-propane sultone to form the desired silyl ligand, where the formed silyl ligand includes a reversed phase (hydrophobic) moiety and a zwitterionic moiety;
2. then allowing the formed silyl ligand to react with the substrate surface to form the chromatographic material by covalent bonding.

General Method 3:

comprising:

1. covalently attaching a silyl ligand containing an alkyl or aryl halide to the substrate surface;
2. then allowing the covalently attached silyl ligand to react with a chemical containing both an amino functionality and a negatively charged moiety to form the chromatographic material, the negatively charged moiety selected from the group consisting of a sulfonate, a carboxylate, and a phosphonate functional group.

General Method 4:

comprising:

1. allowing a silyl ligand containing an alkyl or aryl halide to react with a chemical containing both an amino functionality and a negatively charged moiety selected from the group consisting of a sulfonate, a carboxylate, and a phosphonate functional group to form a zwitterionic ligand;
2. then allowing the zwitterionic ligand to react with the substrate surface by covalent bonding, to form the chromatographic material.

Accordingly, the invention provides:

i. A method of preparing a chromatographic material comprising: covalently attaching a silyl ligand containing an alkyl or aryl moiety and an amino functional group to a substrate surface by covalent bonding; then allowing the covalently attached silyl ligand to react with 1,3-propane sultone to form the chromatographic material.

The substrate is preferably silica and the silyl ligand may have a general formula:

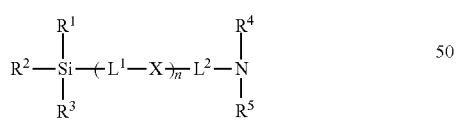

wherein $L^1$ and/or $L^2$ contains an alkyl or aryl moiety.

ii. A method of preparing a chromatographic material comprising: allowing a silyl ligand containing an alkyl or aryl moiety and an amino functional group to react with 1,3-propane sultone to form a silyl ligand consisting of both reversed phase (hydrophobic) moiety and zwitterionic moiety; then allowing the resulting ligand having both reversed phase (hydrophobic) moiety and zwitterionic moiety to react with a substrate surface to form the chromatographic material by covalent bonding.

The substrate is preferably silica and the first silyl ligand may have a general formula:

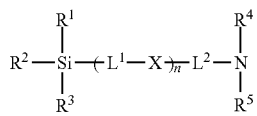

wherein $L^1$ and/or $L^2$ contains an alkyl or aryl moiety, which is reacted with, 3-propane sultone to form a silyl ligand of general formula:

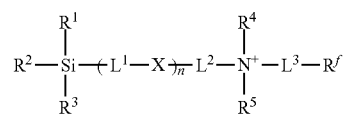

iii. A method of preparing a chromatographic material comprising: covalently attaching a silyl ligand containing an alkyl or aryl halide to a substrate surface; then allowing the covalently attached silyl ligand to react with a chemical containing both amino functionality and negatively charged moiety (or alternatively to the latter a functionality that can be converted to sulfonate (or carboxylate or phosphonate) functionality, for example thiol that can be converted to sulfonate) to form the chromatographic material. The negatively charged moiety is selected from the group consisting of a sulfonate, a carboxylate, and a phosphonate functional group.

The substrate is preferably silica and the silyl ligand may have a general formula:

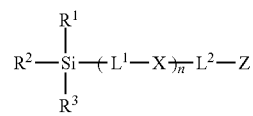

wherein $L^1$ and/or $L^2$ contains an alkyl or aryl moiety, and Z is a halogen atom. The chemical containing both amino functionality and a negatively charged moiety, may have a general formula:

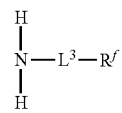

wherein the $R^f$ group can also be a group that can be converted to a negatively charged moiety, for example a thiol group that can be converted to sulfonate. The negatively charged moiety is selected from the group consisting of a sulfonate, a carboxylate, and a phosphonate functional group. The method may also comprise alkylating, e.g. methylating, the amino group to form the cationic amino group —$N^+R^4R^5$.

iv. A method of preparing a chromatographic material comprising: allowing a silyl ligand containing an alkyl or aryl halide to react with a chemical containing both amino functionality and negatively charged moiety to form a zwitterionic ligand; then allowing the resulting zwitterionic ligand to react with a substrate surface by covalent bonding, to form the chromatographic material. The negatively charged moiety is selected from the group consisting of a sulfonate, a carboxylate, and a phosphonate functional group.

v. A method of preparing a chromatographic material comprising: covalently attaching a silyl ligand containing an alkyl amine or aryl amine to a substrate surface; then allowing the alkyl amine or aryl amine contained on the covalently attached silyl ligand to react with a chemical containing both a halide and a negatively charged moiety (or alternatively to the latter of a functionality that can be converted to sulfonate (or carboxylate or phosphonate) functionality, for example thiol that can be converted to sulfonate) to form the chromatographic material. The negatively charged moiety is selected from the group consisting of a sulfonate, a carboxylate, and a phosphonate functional group.

vi. A method of preparing a chromatographic material comprising: allowing a silyl ligand containing an alkyl or aryl amine to react with a chemical containing both a halide functionality and sulfonate (or carboxylate or phosphonate) functionality to form a zwitterionic ligand; then allowing the resulting zwitterionic ligand to react with a substrate surface by covalent bonding, to form the chromatographic material.

vii. A method of preparing a chromatographic material comprising: covalently attaching a silyl ligand containing a thiol or a hydroxyl group to a substrate surface; then allowing the thiol or the hydroxyl group contained on the covalently attached silyl ligand to react with a chemical containing both amino functionality and a negatively charged moiety, optionally also having a vinyl or allyl group, to form the chromatographic material. The negatively charged moiety is selected from the group consisting of a sulfonate, a carboxylate, and a phosphonate functional group.

In the above methods, there may be additional steps such as alkylating, e.g. methylating, the amino group to form a cationic amino group —$N^+R^4R^5$; and converting a thiol group into a sulfonate group.

The material of the invention may be used in nano-LC, analytical-LC, or preparative scale LC, or SPE. In various embodiments, the material is disposed as a packed bed or monolith in a column. For example, a plastic or metal column is packed with the material.

The materials can provide a variety of high-performance separation media. In some embodiments, depending on the pH of the mobile phase in a chromatographic separation, the material may behave as RP material, RP with a slight anion-interaction mixed-mode material, or RP with a slight cation-interaction mixed-mode material. The material has numerous benefits, such as unique selectivity for a broad range of applications, flexible chemistry such that depending on specific applications the surface chemistry can be tailored accordingly. The material has the capability to separate both hydrophobic and ionic analytes with good efficiency.

EXAMPLES

In order to enable further understanding of the invention, but without limiting the scope thereof, various exemplary and/or preferred embodiments of the invention are now described with reference to the accompanying drawings.

Example 1

Referring to FIG. 1:

Synthesis of 2:

To a stirred solution of 22.3 g (0.1 mol, 1.0 equiv) of 1-bromo-undecene 1 (e.g., Aldrich) in a 250 mL round bottom flask under a $N_2$ atmosphere was carefully added 150 mL of 2M dimethylamine in methanol (0.3 mol, 3 molar equiv, e.g., Tokyo Chemical Industry (TCI)). The resulting reaction mixture was stirred at room temperature for 36 h. The reaction was monitored using gas chromatography. When the starting material 1 was found to be consumed completely by GC, all volatiles were removed in vacuum. Compound 2 was obtained by Kugelrohr Distillation (140° C./0.11 torr). Yield: 17.2 g, 90%.

Synthesis of 3:

To a stirred solution of 22.3 g (0.1 mol, 1.0 equiv) of 1-bromo-undecene 1 (e.g., Aldrich), 31 g (0.3 mol, 3.0 equiv) of $(MeO)_2MeSiH$ (e.g., Gelest) in 30 mL of toluene in a 1-L round bottom flask at ambient temperature were carefully added 0.5 g of Pt(0) catalyst (0.15% wt) (e.g., Gelest). Occasionally, an exothermic reaction was observed upon addition of the catalyst. The flask was equipped with a condenser and the reaction mixture was heated to 50° C. for 8 h. The reaction was monitored using gas chromatography. When the conversion was found to be higher than 60% by GC, all volatiles were removed in vacuo. Compound 3 was obtained by Kugelrohr Distillation (120° C./0.05 torr).

Synthesis of 4:

To a stirred solution of 33.9 g (0.1 mol, 1.0 equiv) of 3 in a 500 mL round bottom flask under a $N_2$ atmosphere was carefully added 150 mL of 2M dimethylamine in methanol (0.3 mol, 3 molar equiv, e.g., TCI). The resulting reaction mixture was stirred at room temperature for 36 h. The reaction was monitored using gas chromatography. When the starting material 3 was found to be consumed completely by GC, all volatiles were removed in vacuum. Compound 4 was obtained by Kugelrohr Distillation (160° C./0.11 torr). Yield: 27 g, 90%.

Synthesis of 5:

To a stirred solution of 19.7 g (0.1 mol, 1.0 equiv) of 2 in 500 ml of acetonitrile in a 1 L flask under a $N_2$ atmosphere was carefully added 12.2 g (0.1 mol, 1.0 equiv.) of 1,3-propanesultone (e.g., Aldrich). The reaction mixture was heated to 50° C. for 48 h. Then the solvent was removed under vacuum. The product (5) was washed with acetonitrile and dried under vacuum to yield 28.7 g (0.085 mol, 85%) as a colorless powder.

Synthesis of 6:

Method 1 (from 5): To a stirred solution of 32 g of 5 (0.1 mol, 1.0 equiv), 31 g of $(MeO)_2MeSiH$ (e.g., Gelest) in 30 mL of toluene in a 1-L round bottom flask at ambient temperature were carefully added 0.5 g of Pt(0) catalyst (0.1% wt) (e.g., Gelest). Occasionally, an exothermic reaction was observed upon addition of the catalyst. The flask was equipped with a condenser and the reaction mixture was heated to 50° C. for 8 h. The reaction was monitored using gas chromatography. When the conversion was found to be higher than 60% by GC, all volatiles were removed in vacuo. Silyl ligand 6 was filtered and washed with acetonitrile to yield 36.1 g (0.085 mol) as a colorless powder.

Method 2 (from 4): To a stirred solution of 30.3 g (0.1 mol, 1.0 equiv) of 4 in 500 ml of acetonitrile in a 1 L flask under a $N_2$ atmosphere was carefully added 12.2 g (0.1 mol, 1.0 equiv.) of 1,3-propanesultone (e.g., Aldrich). The reaction mixture was heated to 50° C. for 48 h. Then the solvent was removed under vacuum. The product 6 was washed with acetonitrile and dried under vacuum to yield 28.7 g (0.068 mol, 80%) as a colorless powder.

Preparation of Phase 23b:

20 g of dried porous spherical silica particles (particle size, 5-μm; pore size, 120-Å; surface area, 300 m²/g, silanol: 0.048 mol) was transferred into a 250-mL round bottom flask followed by the addition of a solution of 24 g silyl ligand 6 (0.054 mol) in toluene (50 mL). After carefully dispersing above slurry, the reaction mixture was put under stable refluxing and stirred for 48 h. The functionalized silica particles were filtered and thoroughly washed with toluene and acetone to give Phase 23b.

Preparation of Phase 21:

20 g of dried porous spherical silica particles (particle size, 5-μm; pore size, 120-Å; surface area, 300 m²/g, silanol: 0.048 mol) was transferred into a 250-mL round bottom flask followed by the addition of a solution of 18.3 g silyl ligand 3 (0.054 mol) in toluene (50 mL). After carefully dispersing above slurry, the reaction mixture was put under stable refluxing and stirring for 48 h. The functionalized silica particles were filtered and thoroughly washed with toluene and acetone to give Phase 21.

Preparation of Phase 22:

Method 1 (from 21): 20 g of synthesized silica 21 was transferred into a 250-mL round bottom flask followed by the addition of 2M dimethylamine in THF (36 mL). After carefully dispersing above slurry, the reaction mixture was stirred at room temperature under $N_2$ atmosphere overnight. The functionalized silica particles were filtered and thoroughly washed with toluene and acetone to give Phase 22.

Method 2 (from 4): 20 g of dried porous spherical silica particles (particle size, 5-μm; pore size, 120-Å; surface area, 300 m²/g, silanol: 0.048 mol) was transferred into a 250-mL round bottom flask followed by the addition of a solution of 16.3 g (0.054 mol) of 4 in toluene (50 mL). After carefully dispersing above slurry, the reaction mixture is put under stable refluxing and stirring for 48 h. The functionalized silica particles are filtered and thoroughly washed with toluene and acetone to give Phase 22.

Preparation of Phase 23a:

20 g of synthesized silica 22 was transferred into a 250-mL round bottom flask followed by the addition of a solution of 5.9 g (0.048 mol) of 1,3-propanesultone (e.g., Aldrich) in acetonitrile (100 mL). The reaction mixture was heated to 50° C. for 48 h. The functionalized silica particles are filtered and thoroughly washed with toluene and acetone to give Phase 23a.

Example 2

Figure 2:
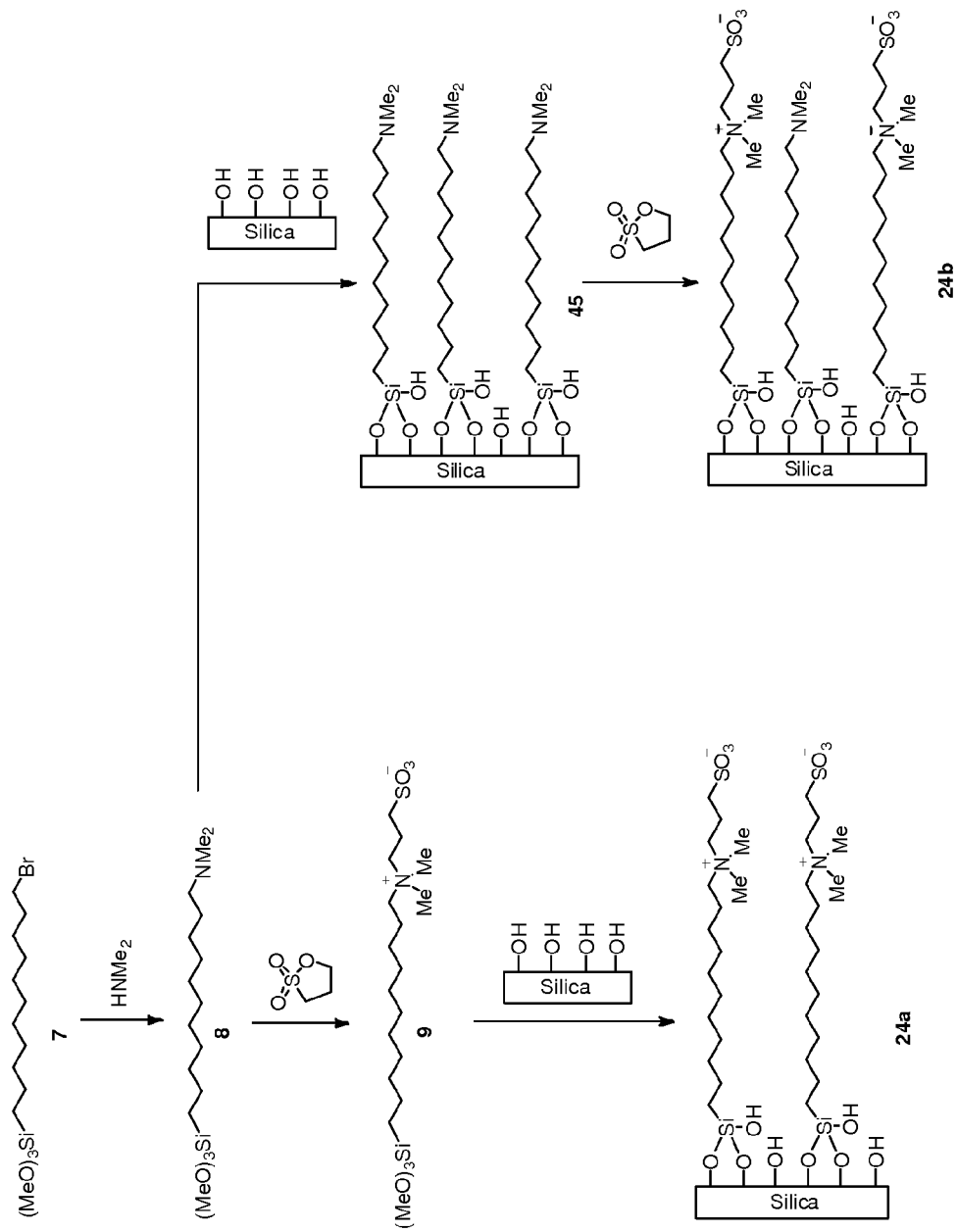
FIG. 2 shows another set of embodiments of routes to preparing materials of the present invention.

Referring to FIG. 2:

Synthesis of 8:

To a stirred solution of 21.3 g (0.06 mol, 1.0 equiv) of 11-Bromoundecyltrimethoxysilane 7 in a 500 mL round bottom flask under a $N_2$ atmosphere was carefully added 90 mL of 2M dimethylamine in methanol (0.18 mol, 3 molar equiv, e.g., TCI). The resulting reaction mixture was stirred at room temperature for 36 h. The reaction was monitored using gas chromatography. When the silane starting material was found to be consumed completely by GC, all volatiles were removed in vacuum. Compound 8 was obtained by Kugelrohr Distillation (160° C./0.11 torr). Yield: 17.2 g, 90%.

Synthesis of 9:

To a stirred solution of 31.9 g (0.1 mol, 1.0 equiv) of 8 in 500 ml of acetonitrile in a 1 L flask under a $N_2$ atmosphere was carefully added 12.2 g (0.1 mol, 1.0 equiv.) of 1,3-propanesultone (e.g., Aldrich). The reaction mixture was heated to 50° C. for 48 h. Then the solvent was removed under vacuum. The product was washed with acetonitrile and dried under vacuum to yield 37.5 g (0.085 mol, 85%) as a colorless powder.

Preparation of Phase 24a:

20 g of dried porous spherical silica particles (particle size, 5-μm; pore size, 120-Å; surface area, 300 m²/g, silanol: 0.048 mol) was transferred into a 250-mL round bottom flask followed by the addition of a solution of 23.8 g (0.054 mol) silyl ligand 9 in toluene (50 mL). After carefully dispersing above slurry, the reaction mixture was put under stable refluxing and stirred for 48 h. The functionalized silica particles were filtered and thoroughly washed with toluene and acetone to give Phase 24a.

Preparation of Phase 45:

20 g of dried porous spherical silica particles (particle size, 5-μm; pore size, 120-Å; surface area, 300 m²/g, silanol: 0.048 mol) was transferred into a 250-mL round bottom flask followed by the addition of a solution of 17.23 g (0.054 mol) silyl ligand 8 in toluene (50 mL). After carefully dispersing above slurry, the reaction mixture was put under stable refluxing and stirring for 48 h. The functionalized silica particles were filtered and thoroughly washed with toluene and acetone to give Phase 45.

Preparation of Phase 24b:

20 g of synthesized silica 45 was transferred into a 250-mL round bottom flask followed by the addition of a solution of 5.9 g (0.048 mol) 1,3-propanesultone (e.g., Aldrich) in acetonitrile (100 mL). The reaction mixture was heated to 50° C. for 48 h. The functionalized silica particles were filtered and thoroughly washed with toluene and acetone to give Phase 24b.

Example 3

Figure 3:
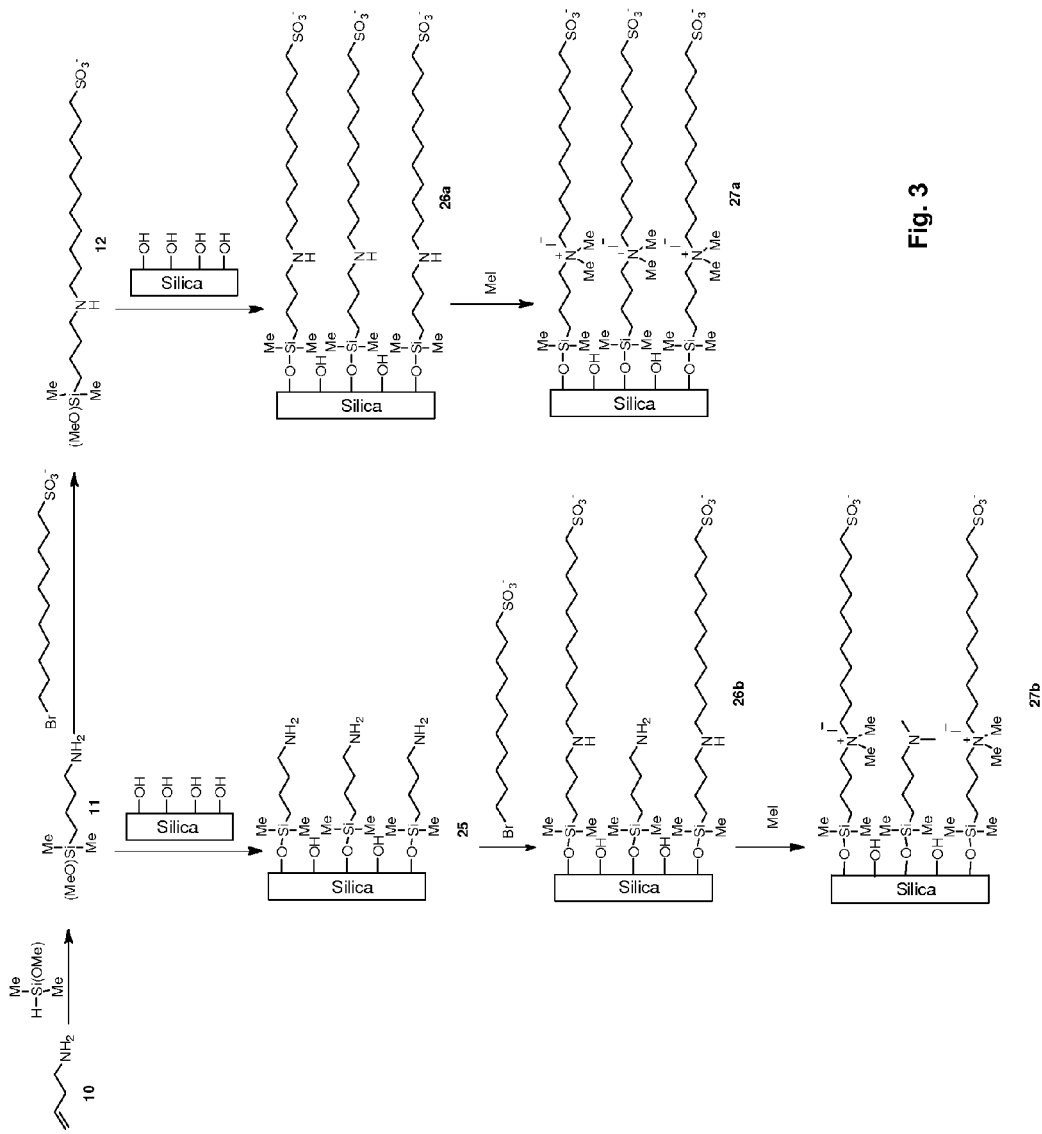
FIG. 3 shows yet another set of embodiments of routes to preparing materials of the present invention.

Referring to FIG. 3:

Synthesis of 11:

To a stirred solution of 11.4 g (0.16 mol) but-3-en-1-amine (e.g., Aldrich), 45.1 g (0.47 mol) of $(MeO)Me_2SiH$ (e.g., Gelest) in 20 mL of toluene in a 250 mL round bottom flask at ambient temperature were carefully added 0.05 g of Pt(0) catalyst (0.1% wt) (e.g., Gelest). Occasionally, an exothermic reaction is observed upon addition of the catalyst. The flask was equipped with a condenser and the reaction mixture was heated to 50° C. for 8 h. The reaction was monitored using gas chromatography. When the conversion was found to be higher than 60% by GC, all volatiles were removed in vacuo. Compound 11 was obtained by Kugelrohr Distillation (100° C./0.11 torr).

Synthesis of 12:

To a stirred solution of 9.66 g (0.06 mol, 1.0 equiv) 11 in a 500 mL round bottom flask under a $N_2$ atmosphere was carefully added 56.5 g (0.18 mol, 3 molar equiv, e.g., TCI) 11-bromoundecane-1-sulfonate. The resulting reaction mixture was stirred at room temperature for 36 h. The reaction was monitored using gas chromatography. When the silane starting material was found to be consumed completely by GC, all volatiles were removed in vacuum. Compound 12 was obtained by Kugelrohr Distillation (160° C./0.11 torr).

Preparation of Phase 25

20 g of dried porous spherical silica particles (particle size, 5-μm; pore size, 120-Å; surface area, 300 m²/g, silanol: 0.048 mol) was transferred into a 250-mL round bottom flask followed by the addition of a solution 8.7 g (0.054 mol) silyl ligand 11 in toluene (50 mL). After carefully dispersing above slurry, the reaction mixture was put under stable refluxing and stirred for 48 h. The functionalized silica particles were filtered and thoroughly washed with toluene and acetone to give Phase 25.

Preparation of Phase 26a:

20 g of dried porous spherical silica particles (particle size, 5-µm; pore size, 120-Å; surface area, 300 m$^2$/g, silanol: 0.048 mol) was transferred into a 250-mL round bottom flask followed by the addition of a solution of 21.3 g (0.054 mol) 12 in toluene (60 mL). After carefully dispersing above slurry, the reaction mixture was put under stable refluxing and stirred for 48 h. The functionalized silica particles were filtered and thoroughly washed with toluene and acetone to give Phase 26a.

Preparation of Phase 26b:

20 g of synthesized silica 25 was transferred into a 250-mL round bottom flask followed by the addition of a solution of 45.2 g (0.144 mol) 11-bromoundecane-1-sulfonate in THF (75 mL). After carefully dispersing above slurry, the reaction mixture was stirred at room temperature under N$_2$ atmosphere overnight. The functionalized silica particles were filtered and thoroughly washed with toluene and acetone to give Phase 26b.

Preparation of Phase 27a:

20 g of synthesized silica 26a was transferred into a 250-mL round bottom flask followed by the addition of a solution of 14.2 g (0.1 mol) CH$_3$I in MeOH (75 mL) ("MeI"). After carefully dispersing above slurry, the reaction mixture was stirred at room temperature under N$_2$ atmosphere overnight. The functionalized silica particles were filtered and thoroughly washed with toluene and acetone to give Phase 27a.

Preparation of Phase 27b 20 g of synthesized silica 26b was transferred into a 250-mL round bottom flask followed by the addition of a solution of 14.2 g (0.1 mol) CH$_3$I in MeOH (75 mL). After carefully dispersing above slurry, the reaction mixture was stirred at room temperature under N$_2$ atmosphere overnight. The functionalized silica particles were filtered and thoroughly washed with toluene and acetone to give Phase 27b.

Example 4

Figure 4:
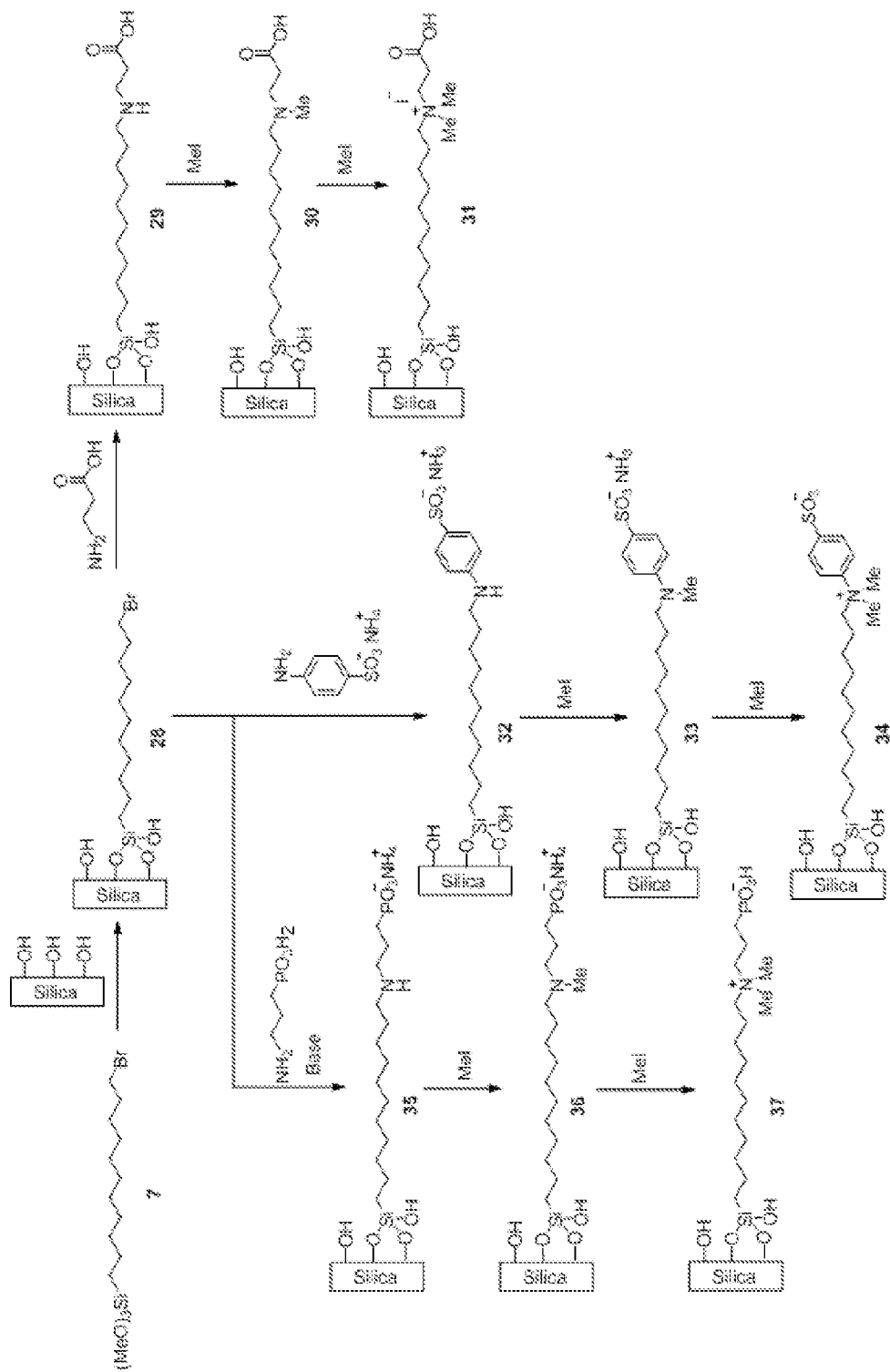
FIG. 4 shows still another set of embodiments of routes to preparing materials of the present invention.

Referring to FIG. 4:

Preparation of Phase 28:

20 g of dried porous spherical silica particles (particle size, 5-µm; pore size, 120-Å; surface area, 300 m$^2$/g, silanol: 0.048 mol) was transferred into a 250-mL round bottom flask followed by the addition of a solution of 19.2 g (0.054 mol) silyl ligand 7 in toluene (50 mL). After carefully dispersing above slurry, the reaction mixture was put under stable refluxing and stirred for 48 h. The functionalized silica particles were filtered and thoroughly washed with toluene and acetone to give Phase 28.

Preparation of Phase 29;

20 g of synthesized silica 28 transferred into a 250-mL round bottom flask followed by the addition of a solution of 4.3 g (0.054 mmol) 3-aminopropanoic acid (e.g., Aldrich) in acetonitrile (100 mL). After carefully dispersing above slurry, the reaction mixture was heated to 50° C. for 48 h. The functionalized silica particles were filtered and thoroughly washed with toluene and acetone to give Phase 29.

Preparation of Phase 30:

20 g of synthesized silica 29 was transferred into a 250-mL round bottom flask followed by the addition of a solution of 7.1 g (0.05 mol) CH$_3$I in MeOH (75 mL). After carefully dispersing above slurry, the reaction mixture was stirred at room temperature under N$_2$ atmosphere overnight. The functionalized silica particles were filtered and thoroughly washed with toluene and acetone to give Phase 30.

Preparation of Phase 31:

20 g of synthesized silica 30 was transferred into a 250-mL round bottom flask followed by the addition of a solution of 7.1 g (0.05 mol) CH$_3$I in MeOH (75 mL). After carefully dispersing above slurry, the reaction mixture was stirred at room temperature under N$_2$ atmosphere overnight. The functionalized silica particles were filtered and thoroughly washed with toluene and acetone to give Phase 31.

Preparation of Phase 32:

20 g of synthesized silica 28 was transferred into a 250-mL round bottom flask followed by the addition of a solution of 15.8 g (0.054 mmol) ammonium 4-aminobenzene-sulfonate (e.g., Aldrich) in acetonitrile (100 mL). The reaction mixture was heated to 50° C. for 48 h. The functionalized silica particles were filtered and thoroughly washed with toluene and acetone to give Phase 32.

Preparation of Phase 33:

20 g of synthesized silica 32 was transferred into a 250-mL round bottom flask followed by the addition of a solution of 7.1 g (0.05 mol) CH$_3$I in MeOH (75 mL). After carefully dispersing above slurry, the reaction mixture was stirred at room temperature under N$_2$ atmosphere overnight. The functionalized silica particles were filtered and thoroughly washed with toluene and acetone to give Phase 33.

Preparation of Phase 34:

20 g of synthesized silica 33 was transferred into a 250-mL round bottom flask followed by the addition of a solution of 7.1 g (0.05 mol) CH$_3$I in MeOH (75 mL). After carefully dispersing above slurry, the reaction mixture was stirred at room temperature under N$_2$ atmosphere overnight. The functionalized silica particles were filtered and thoroughly washed with toluene and acetone to give Phase 34.

Preparation of Phase 35:

20 g of synthesized silica 28 was transferred into a 250-mL round bottom flask followed by the addition of a mixture of 8.5 g sodium carbonate (0.081 mol), 7.4 g (0.054 mol) of 3-aminopropylphosphonic acid (e.g., Aldrich) in acetonitrile and water (100 mL, 1:1 v/v). The reaction mixture was heated to 100° C. for 48 h. After cooling, the functionalized silica particles were filtered and thoroughly washed with toluene and acetone to give Phase 35.

Preparation of Phase 36:

20 g of synthesized silica 35 was transferred into a 250-mL round bottom flask followed by the addition of a solution of 7.1 g (0.05 mol) CH$_3$I in MeOH (75 mL). After carefully dispersing above slurry, the reaction mixture was stirred at room temperature under N$_2$ atmosphere overnight. The functionalized silica particles were filtered and thoroughly washed with toluene and acetone to give Phase 36.

Preparation of Phase 37:

20 g of synthesized silica 36 was transferred into a 250-mL round bottom flask followed by the addition of a solution of 7.1 g (0.05 mol) CH$_3$I in MeOH (75 mL). After carefully dispersing above slurry, the reaction mixture was stirred at room temperature under N$_2$ atmosphere overnight. The functionalized silica particles were filtered and thoroughly washed with toluene and acetone to give Phase 37.

Example 5

Figure 5:
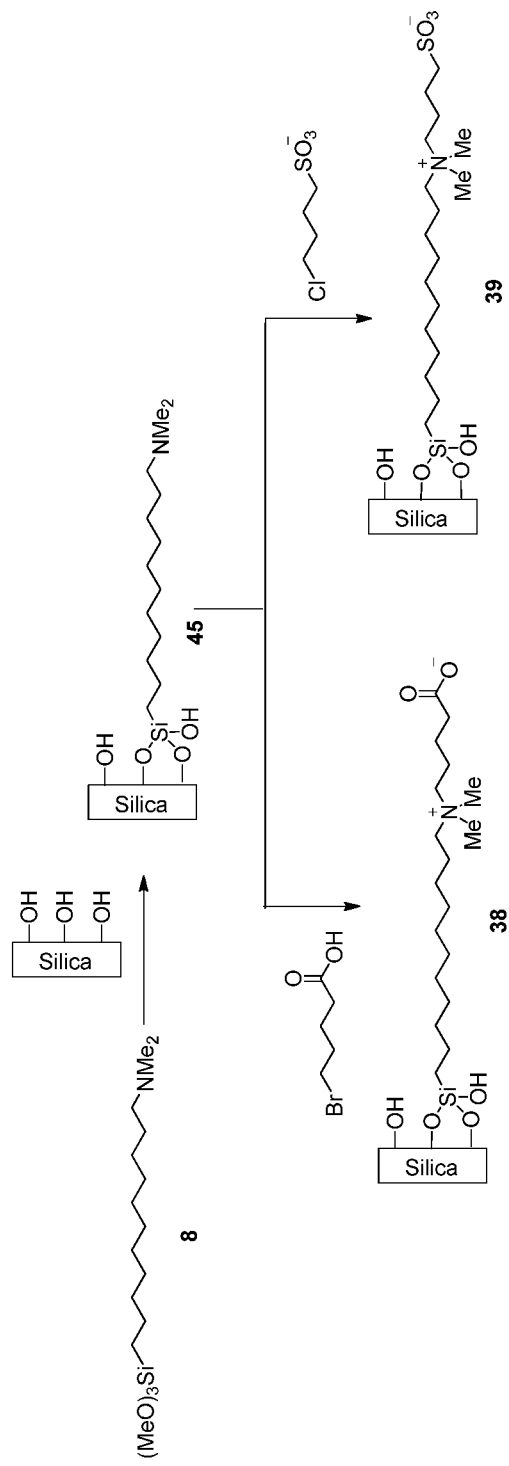
FIG. 5 shows a further set of embodiments of routes to preparing materials of the present invention.

Referring to FIG. 5:

Preparation of Phase 38:

20 g of synthesized silica 45 was transferred into a 250-mL round bottom flask followed by the addition of a solution of 9.8 g (0.054 mol) 5-bromopentanoic acid (e.g., Aldrich) in acetonitrile (100 mL). The reaction mixture was heated to 50° C. for 48 h. The functionalized silica particles were filtered and thoroughly washed with toluene and acetone to give Phase 38.

Preparation of Phase 39:

20 g of synthesized silica 45 was transferred into a 250-mL round bottom flask followed by the addition of a solution of 9.32 g (0.054 mol) of 4-chlorobutane-1-sulfonic acid (e.g., Aldrich) in acetonitrile (100 mL). The reaction mixture was heated to 50° C. for 48 h. The functionalized silica particles are filtered and thoroughly washed with toluene and acetone to give Phase 39.

Example 6

Figure 6:
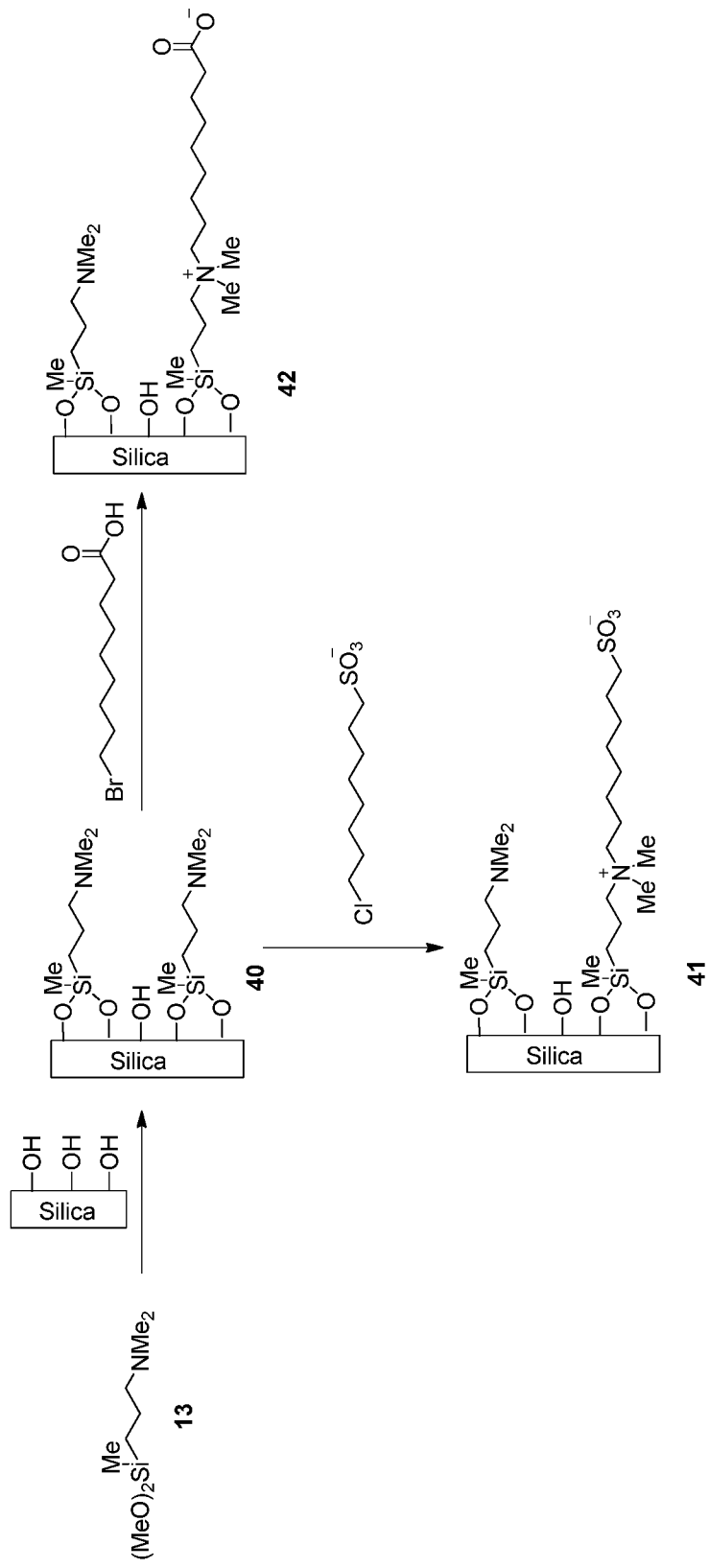
FIG. 6 shows a still further set of embodiments of routes to preparing materials of the present invention.

Referring to FIG. 6:

Preparation of Phase 40:

20 g of dried porous spherical silica particles (particle size, 5-μm; pore size, 120-Å; surface area, 300 m$^2$/g, silanol: 0.048 mol) was transferred into a 250-mL round bottom flask followed by the addition of a solution of 9.2 g 3-(dimethoxy(methyl)silyl)-N,N-dimethylpropan-1-amine 13 (0.054 mol) in toluene (50 mL). After carefully dispersing above slurry, the reaction mixture was put under stable refluxing and stirred for 48 h. The functionalized silica particles were filtered and thoroughly washed with toluene and acetone to give Phase 40.

Preparation of Phase 41:

20 g of synthesized silica 40 was transferred into a 250-mL round bottom flask followed by the addition of a solution of 14.72 g (0.054 mol) 8-chlorooctane-1-sulfonic acid (e.g., Aldrich) in acetonitrile (100 mL). After carefully dispersing above slurry, the reaction mixture was heated to 50° C. for 48 h. The functionalized silica particles were filtered and thoroughly washed with toluene and acetone to give Phase 41.

Preparation of Phase 42:

20 g of synthesized silica 40 was transferred into a 250-mL round bottom flask followed by the addition of a solution of 12.7 g (0.054 mol) of 9-bromononanoic acid (e.g., Aldrich) in acetonitrile (100 mL). After carefully dispersing above slurry, the reaction mixture was heated to 50° C. for 48 h. The functionalized silica particles were filtered and thoroughly washed with toluene and acetone to give Phase 42.

Example 7

Figure 7:
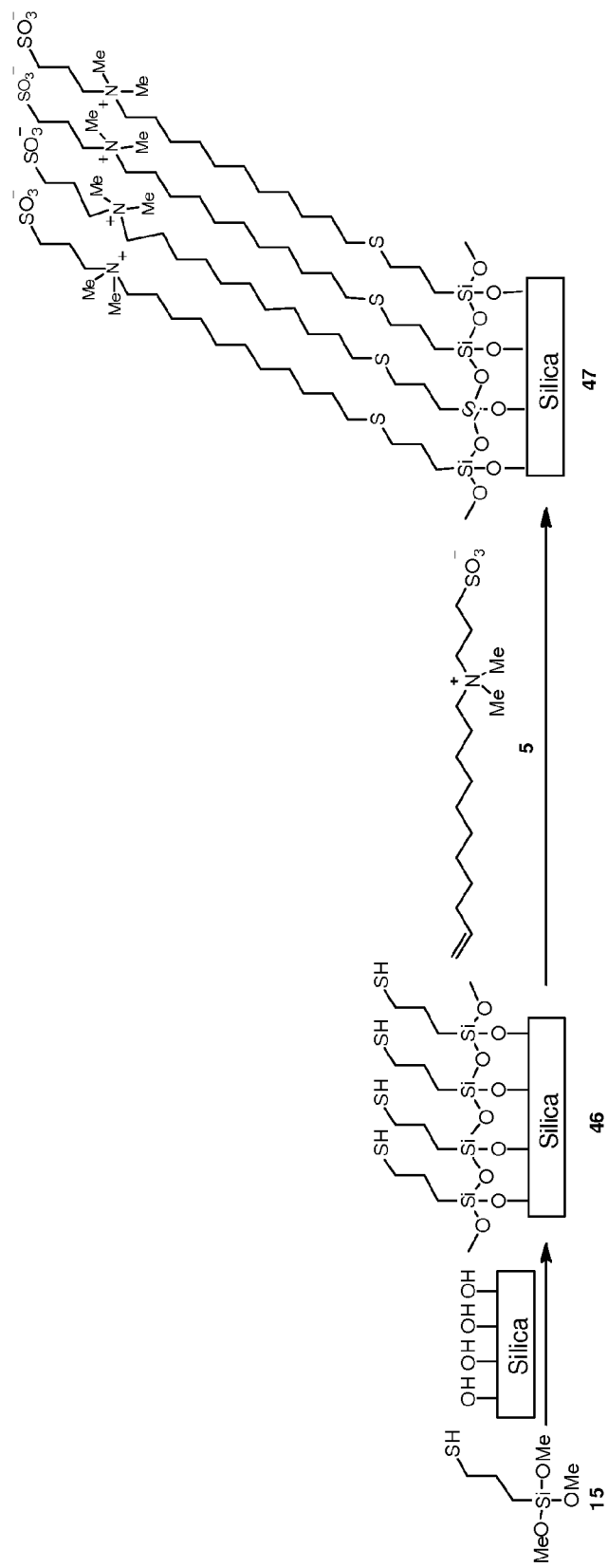
FIG. 7 shows another embodiment of a route to preparing materials of the present invention.

Referring to FIG. 7:

Preparation of Phase 46:

20 g of dried porous spherical silica particles (particle size, 5-μm; pore size, 120-Å; surface area, 300 m$^2$/g, silanol: 0.048 mol) was transferred into a 250-mL round bottom flask followed by the addition of a solution of 10.58 g (0.054 mol, Gelest) of 3-(trimethoxysilyl)-propane-1-thiol 15 in toluene (50 mL). After carefully dispersing above slurry, the reaction mixture was put under stable refluxing and stirred for 72 h. The functionalized silica particles were filtered and thoroughly washed with toluene and acetone to give Phase 46.

Preparation of Phase 47:

5 g of synthesized silica 46, compound 5 (3.83 g, 0.012 mol) and AIBN (1 g, 0.006 mmol) were transferred into a 100-mL round bottom flask followed by the addition of 30 ml of the mixture of methanol-H$_2$O (1:2 v/v). The resulting mixture was heated at 65° C. for 12 h under nitrogen atmosphere. After cooling down, the functionalized silica particles were filtered and thoroughly washed with toluene and acetone to give Phase 47.

Example 8

Figure 8:
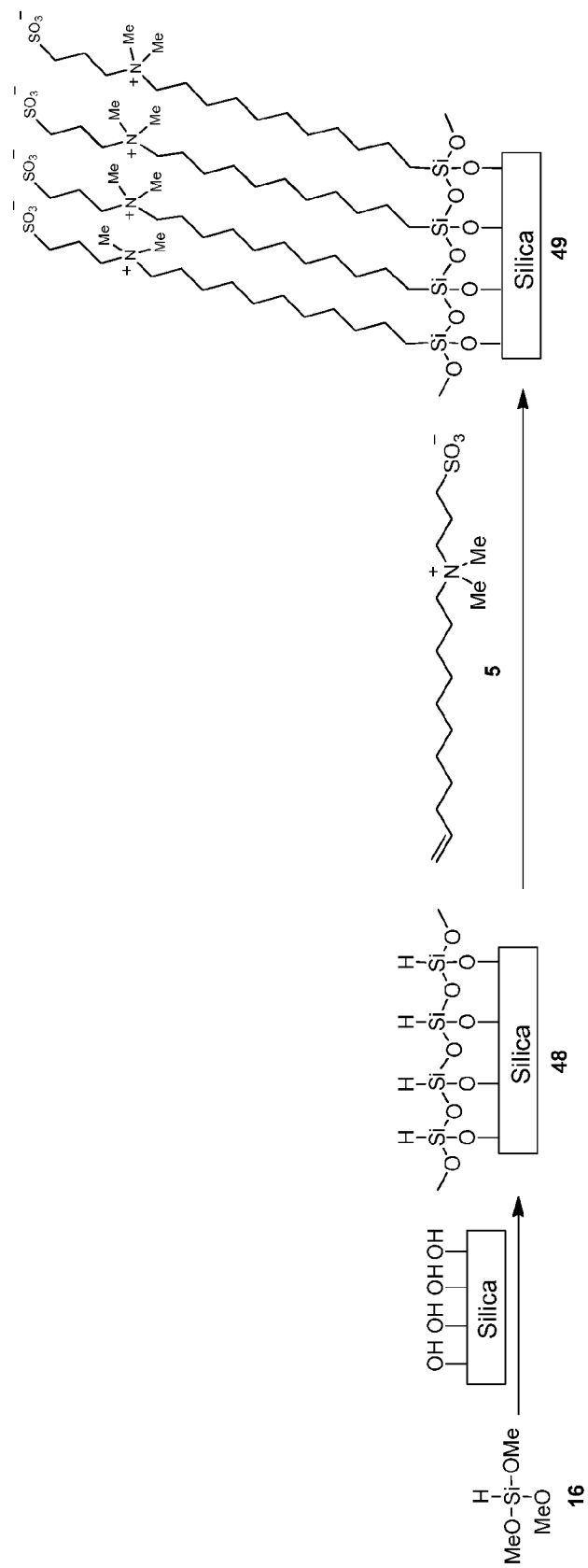
FIG. 8 shows yet another embodiment of a route to preparing materials of the present invention.

Referring to FIG. 8:

Preparation of Phase 48:

20 g of dried porous spherical silica particles (particle size, 5-μm; pore size, 120-Å; surface area, 300 m$^2$/g, silanol: 0.048 mol) was transferred into a 250-mL round bottom flask followed by the addition of a solution of 6.59 g trimethoxysilane 16 (0.054 mol, Gelest) in dry toluene (50 mL). After carefully dispersing above slurry, the reaction mixture was put under stable refluxing and stirred for 72 h. The functionalized silica particles were quickly filtered and washed with toluene and acetone to give Phase 48.

Preparation of Phase 49:

To a stirred solution of 20 g of functionalized silica Phase 48, 13.52 g (0.048 mol) of compound 5 in 90 mL of dry toluene in a 1-L round bottom flask at ambient temperature were carefully added 0.1 g of Pt(0) catalyst (0.1% wt) (e.g., Gelest). Occasionally, an exothermic reaction is observed upon addition of the catalyst. The flask was equipped with a condenser and the reaction mixture was heated at 50° C. for 8 h under nitrogen atmosphere. After all volatiles were removed in vacuo, the silica was washed with a large amount of toluene, acetone and methanol to yield the functionalized silica Phase 49.

Chromatographic Applications

This section describes chromatographic evaluation results. Various bonded phases as described were packed into 3 mm (i.d.)×50, 100 or 150 mm (length) stainless steel columns using traditional high-pressure slurry techniques and subjected to the tests below.

Example 9

Hydrophobicity Test

Figure 9:
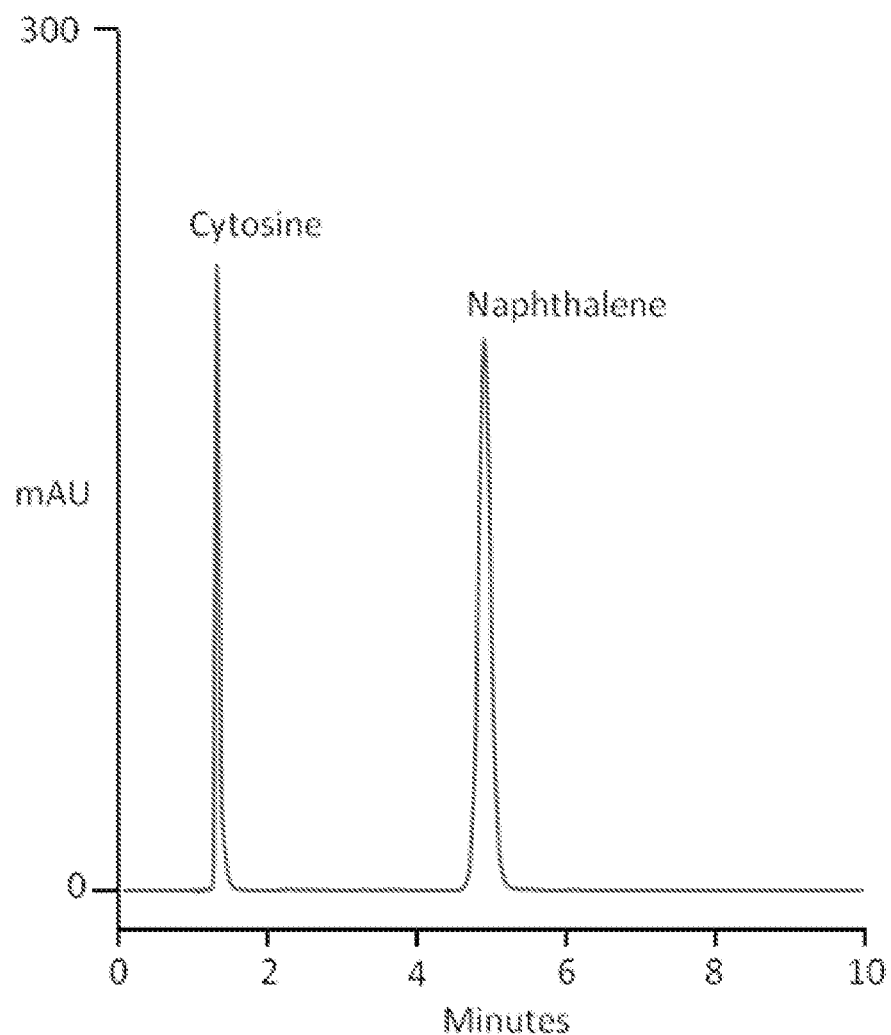

Hydrophobicity is an important parameter to characterize a reversed-phase material, or a mixed mode material having a reversed-phase separation characteristic. FIG. 9 shows the hydrophobicity property of Phase 23a using a hydrophilic void marker (cytosine) and a neutral hydrophobic probe (naphthalene).

The test conditions were: column, packing Phase 23a, particle size 5-μm, column dimensions 3×100-mm; mobile phase: acetonitrile/100 mM ammonium acetate, pH5 (40:60 v/v); flow rate, 0.425 mL/min; injection volume, 2 μL; temperature, 30° C.; detection UV wavelength, 254 nm; and test probes (0.1 mg/mL each in mobile phase), cytosine and naphthalene.

The test probes were clearly separated with the retention of naphthalene indicating that the packing Phase 23a has good reversed-phase separation capability.

Example 10

Ion-Interaction Property

The ion-interaction property was characterized using an anion ($NO_3^-$) and a cation ($Na^+$) in a mobile phase with controlled ionic strength and pH.

The test conditions were: column, packing Phase 23a, particle size 5-μm, column dimensions 3×50-mm; mobile phase: acetonitrile/100 mM ammonium acetate, pH5/D.I. water (80:10:10 v/v/v); flow rate, 0.425 mL/min; injection volume, 1 μL; temperature, 30° C.; detection, aerosol based detector; and test probe (1 mg/mL in mobile phase): $NaNO_3$.

Figure 10:
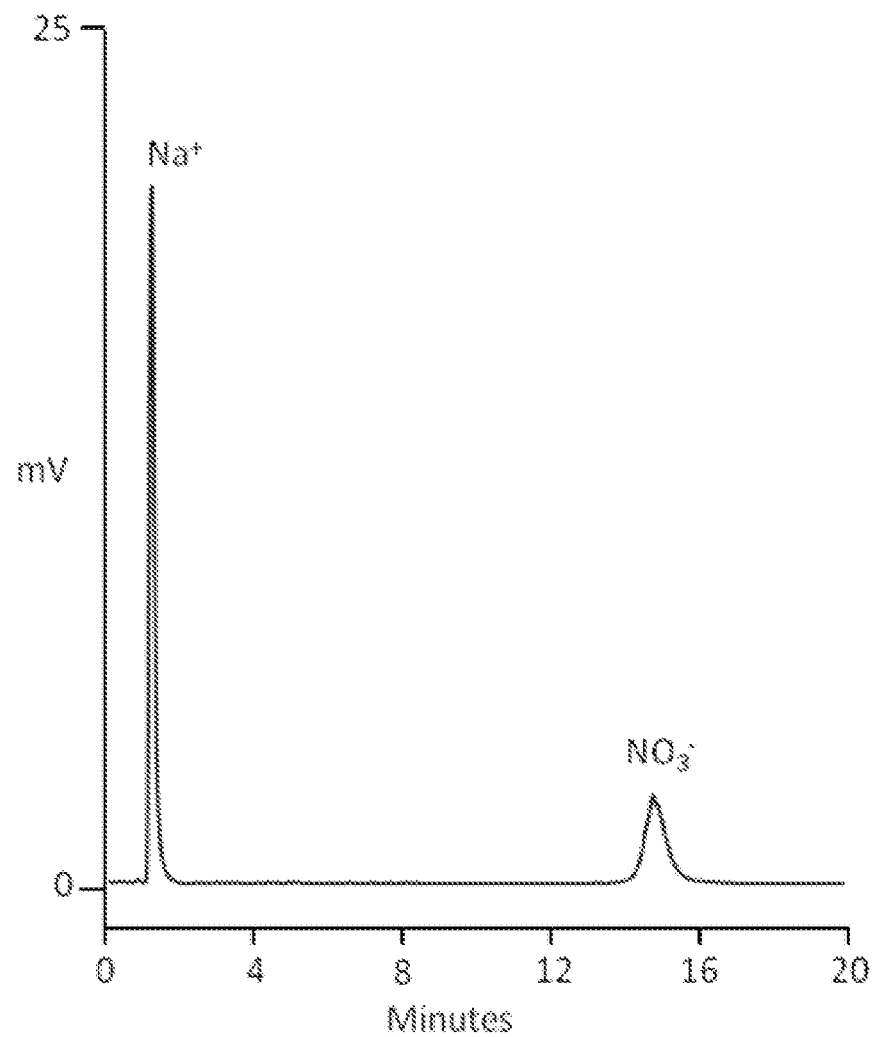

As shown in FIG. 10, Phase 23a exhibits a good anion-interaction property due to the presence of both zwitterionic and amino functionalities on the surface.

Example 11

HILIC Property

Hydrophilic interaction liquid chromatography (HILIC) is commonly used for separation of hydrophilic analytes, as a complementary tool to reverse phase liquid chromatography. Any polar chromatographic surface can be used for HILIC separations. A typical mobile phase for HILIC chromatography includes acetonitrile with a small amount of aqueous portion. In HILIC, the mobile phase forms a water-rich layer on the surface of the polar stationary phase as opposed to the water-deficient mobile phase, creating a liquid/liquid extraction system. The analyte is distributed between these two layers. However, HILIC is a more complicated process than simple partitioning and includes hydrogen bonding interactions between neutral polar species as well as electrostatic interaction under the high organic solvent conditions used for retention. This distinguishes HILIC as a mechanism distinct from ion exchange chromatography. The more polar analytes will have a stronger interaction with the stationary aqueous layer than the less polar ones.

In the evaluation here, mannitol was used to characterize the HILIC property of Phase 23a. The test conditions were: column, packing Phase 23a, particle size 5-μm, column dimensions 3×50-mm; mobile phase: acetonitrile/100 mM ammonium acetate, pH 5/D.I. water (50:10:40 v/v/v) for reverse phase operation, and acetonitrile/100 mM ammonium acetate, pH 5 (90:10 v/v) for HILIC operation; flow rate, 0.425 mL/min; injection volume, 1 μL; temperature, 30° C.; detection, aerosol based detector; and test probe (1 mg/mL in D.I. water): mannitol.

Figure 11:
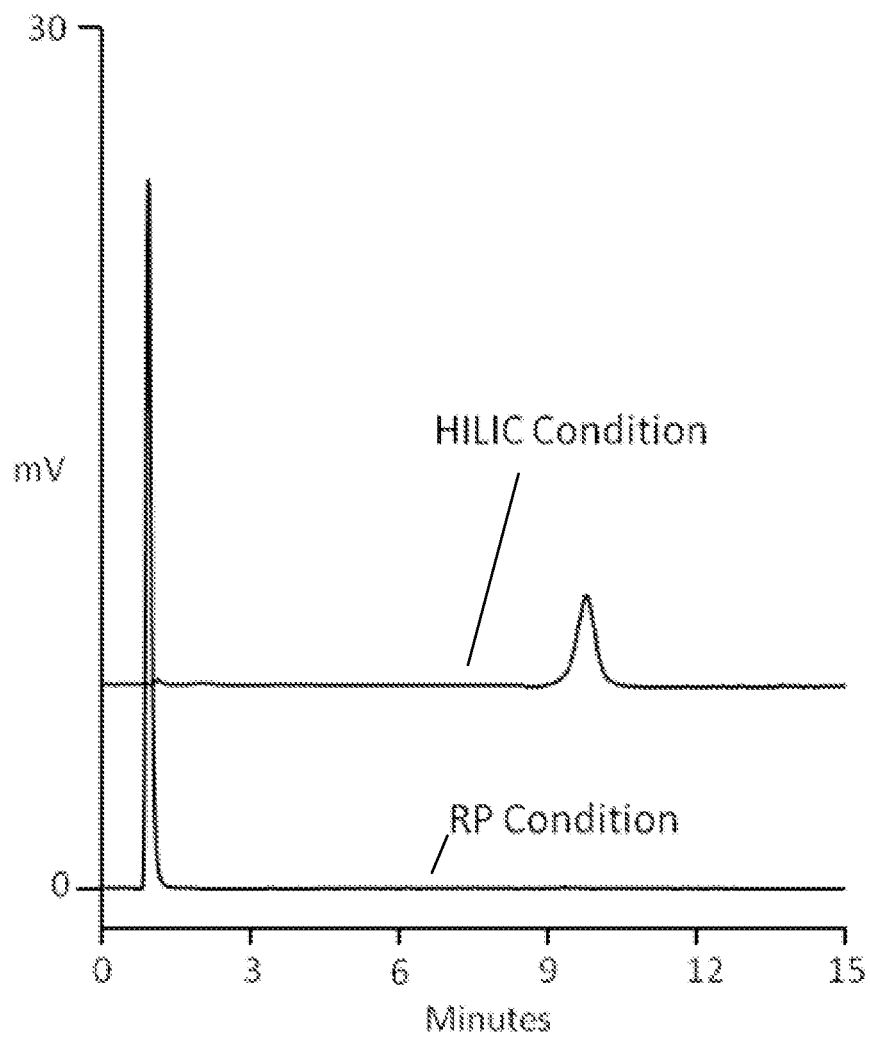

Since mannitol is a highly hydrophilic neutral molecule affected by neither mobile phase ionic strength nor pH (see below), its retention at high acetonitrile levels is considered solely from a hydrophilic interaction without electrostatic interaction. FIG. 11 illustrates clearly that Phase 23a can be used in HILIC to retain hydrophilic analytes by hydrogen bonding interaction as the retention of mannitol at 90% acetonitrile (solvent rich) is significantly higher (retention factor greater than 10) than that at 50% acetonitrile (retention factor close to zero).

Example 12

Solvent Effect

In order to evaluate the chromatographic properties as a reverse phase/zwitterionic mixed-mode phase, naphthalene (hydrophobic probe), mannitol (hydrophilic probe), sodium ion (cation-interaction probe) and chloride (anion-interaction probe) were assessed at different acetonitrile levels and at constant ammonium acetate concentration.

The test conditions were: column, packing Phase 23a, particle size 5-μm, column dimensions 3×50-mm; mobile phase: acetonitrile/100 mM ammonium acetate, pH 5/D.I. water (m:10:n v/v/v, where m:n=90:0, 80:10, 70:20, 60:30, 50:40, 40:50, 30:60, 20:70 and 10:80 ratios); flow rate, 0.425 mL/min; injection volume, 1 μL; temperature, 30° C.; detection, aerosol based detector; and test probes: naphthalene (0.1 mg/mL), sodium chloride (1 mg/mL), and mannitol (1 mg/mL).

Figure 12:
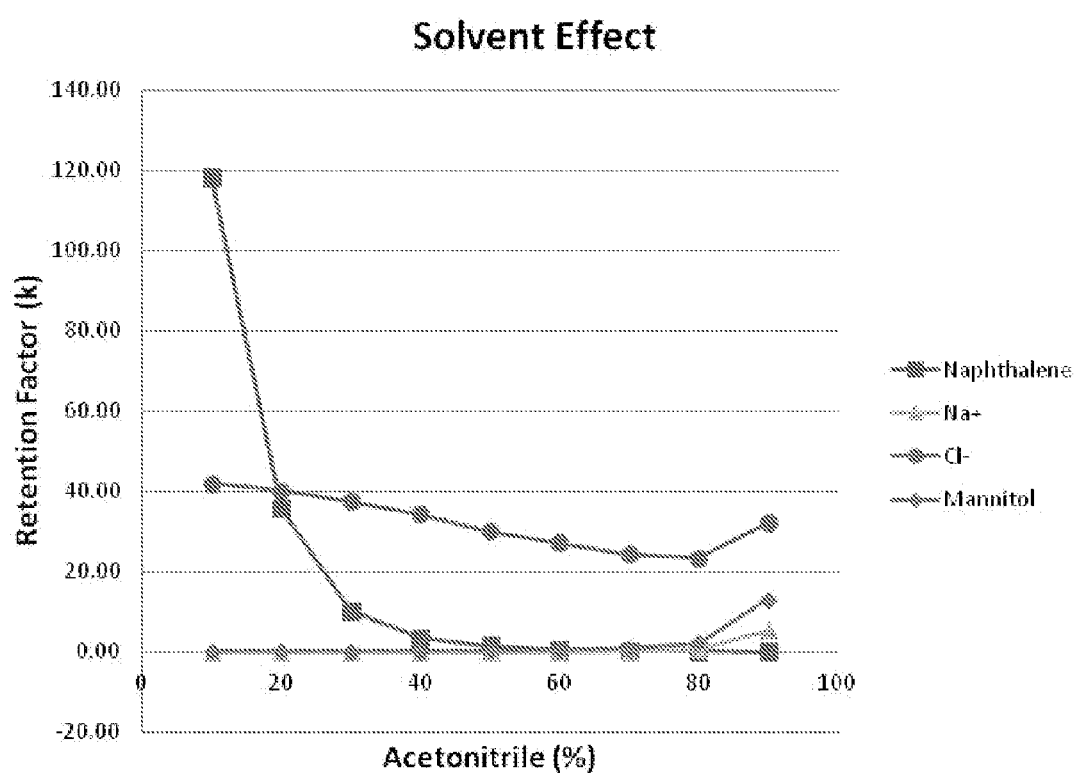

FIG. 12 indicates that Phase 23a exhibits a hydrophobic property as the retention of naphthalene increases continuously with mobile phase aqueous content. At the same time, the retention of mannitol goes in the opposite direction, with minimal retention at acetonitrile content below 70% and increasing with acetonitrile above 70% content. Compared to mannitol, chloride ion shows significantly higher retention at various solvent levels. The retention of chloride decreases continuously with acetonitrile increase, dropping from 41 at 10% acetonitrile down to 20 at 80% acetonitrile. Further increase in acetonitrile results in a rapid chloride retention increase to a value of 33 at 80% acetonitrile. Compared with chloride, sodium ion exhibits virtually no retention in the range of 10% and 80% acetonitrile. Above 80% acetonitrile its retention increases with the solvent content, from a retention of zero to 5.4 at 90% acetonitrile. The results thus indicate that Phase 23a possesses reverse phase, HILIC and anion-interaction properties, which is consistent with its column chemistry.

As used herein, including in the claims, unless the context indicates otherwise, singular forms of the terms herein are to be construed as including the plural form and vice versa. For instance, unless the context indicates otherwise, a singular reference, such as "a" or "an" means "one or more".

Throughout the description and claims of this specification, the words "comprise", "including", "having" and "contain" and variations of the words, for example "comprising" and "comprises" etc, mean "including but not limited to", and are not intended to (and do not) exclude other components.

It will be appreciated that variations to the foregoing embodiments of the invention can be made while still falling within the scope of the invention. Each feature disclosed in this specification, unless stated otherwise, may be replaced by alternative features serving the same, equivalent or similar purpose. Thus, unless stated otherwise, each feature disclosed is one example only of a generic series of equivalent or similar features.

The use of any and all examples, or exemplary language ("for instance", "such as", "for example", "e.g." and like language) provided herein, is intended merely to better illustrate the invention and does not indicate a limitation on the scope of the invention unless otherwise claimed. No language in the specification should be construed as indicating any non-claimed element as essential to the practice of the invention.

Any steps described in this specification may be performed in any order or simultaneously unless stated or the context requires otherwise.

All of the features disclosed in this specification may be combined in any combination, except combinations where at least some of such features and/or steps are mutually exclusive. In particular, the preferred features of the invention are applicable to all aspects of the invention and may be used in any combination. Likewise, features described in non-essential combinations may be used separately (not in combination).

What is claimed is:

1. A chromatographic material comprising a zwitterionic ligand covalently bound to a substrate, wherein the zwitterionic ligand has a general formula I:

wherein the zwitterionic ligand is covalently bound to the substrate through the silyl group, the ionic groups have opposite charges to each other, and there are at least 10 carbon atoms in the combined chain lengths of the hydrophobic linkers, wherein at least one of the hydrophobic linkers comprises a homoalkyl group having at least 8 carbon atoms in the chain.

2. The chromatographic material as claimed in claim 1, wherein the zwitterionic ligand has a formula II:

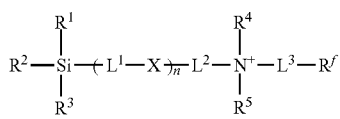

wherein
$R^1, R^2, R^3$ are independently selected from
an oxygen atom that is configured to connect to a substrate atom in the substrate,
an oxygen atom that is configured to connect to a silicon atom of an adjacent ligand,
a hydroxyl group,
a halogen atom,
an alkoxy group,
a dialkylamino group,
an acyl group,
an alkyl group, or
an aryl group;
$L^1$, $L^2$ and $L^3$ are independently hydrophobic moieties; each containing 2 to 30 carbon atoms, wherein there are at least 10 carbon atoms in the combined chain lengths of $L^1$, $L^2$ and $L^3$, wherein at least one of $L^1$, $L^2$ and $L^3$ comprises a homoalkyl group having at least 8 carbon atoms in the chain;
X is an O atom, S atom, amide group or sulfonamide group;
n is 0 or 1;
$R^4$, $R^5$ are independently selected from a hydrogen atom or a hydrocarbon moiety containing 1 to 20 carbon atoms; and
$R_f$ is a negatively charged moiety selected from the group consisting of a sulfonic, carboxylic, and phosphonic functional group.

3. The chromatographic material as claimed in claim 2, wherein the alkoxy group is methoxy, ethoxy or propoxy; the alkyl group is a substituted or unsubstituted alkyl group, or a substituted or unsubstituted heteroalkyl group; the aryl group is a substituted or unsubstituted aryl group, or a substituted or unsubstituted heteroaryl group.

4. The chromatographic material as claimed in claim 2, wherein at least one of $R^1$, $R^2$, $R^3$ groups is a leaving group.

5. The chromatographic material as claimed in claim 1, wherein there are at least 11 carbon atoms in the combined chain lengths of the hydrophobic linkers.

6. The chromatographic material as claimed in claim 1, wherein the hydrophobic linkers are each straight chain homoalkyl groups.

7. The chromatographic material as claimed in claim 1, wherein at least one of the hydrophobic linkers comprises a homoalkyl group having 8 to 12 carbon atoms in the chain.

8. The chromatographic material as claimed in claim 1, wherein the ionic group at a central portion of the zwitterionic ligand is a central ionic group, the central ionic group having a positively charged group, the central portion being in between the two hydrophobic linkers, and the other ionic group at an end portion of the zwitterionic ligand is an end ionic group, the end ionic group having a negatively charged group.

9. The chromatographic material as claimed in claim 2, wherein at least one of $R^1$, $R^2$, $R^3$ groups is an alkoxy group, a dialkylamino group, or a halogen atom.

10. The chromatographic material as claimed in claim 2, wherein $L^1$, $L^2$ and $L^3$ are independently hydrophobic moieties selected from substituted or unsubstituted alkyl and substituted or unsubstituted aryl, wherein there are at least 11 carbon atoms in the combined chain lengths of $L^1$, $L^2$ and $L^3$.

11. The chromatographic material as claimed in claim 2, wherein said hydrocarbon moiety is an alkyl group having 1 to 4 carbon atoms.

12. The chromatographic material as claimed in claim 2, wherein $L^2$ and $L^3$ are each homoalkyl groups.

13. The chromatographic material as claimed in claim 2, wherein at least one of $L^2$ and $L^3$ comprises a homoalkyl group having at least 8 carbon atoms in the chain.

14. The chromatographic material as claimed in claim 2, wherein at least one of $L^2$ and $L^3$ comprises a homoalkyl group having 8 to 12 carbon atoms in the chain.

15. The chromatographic material as claimed in claim 1, wherein the substrate is a silica substrate.

16. A chromatography column packed with the material of claim 1 for use in liquid chromatography or solid phase extraction.

17. A method of preparing a chromatographic material comprising: covalently attaching a silyl ligand containing an alkyl or aryl moiety and an amino functional group to a substrate surface by covalent bonding; then allowing the amino functional group contained on the covalently attached silyl ligand to react with 1,3-propane sultone to form the chromatographic material.

18. A method of preparing a chromatographic material comprising: allowing a silyl ligand containing an alkyl or aryl moiety and an amino functional group to react with 1,3-propane sultone to form a silyl ligand, the formed silyl ligand including a reversed phase moiety and a zwitterionic moiety; then allowing the formed silyl ligand to react with a substrate surface to form the chromatographic material by covalent bonding.

19. A zwitterionic ligand having a general formula I:

wherein the silyl group is an activated silyl group for bonding to a substrate, the ionic groups have opposite charges to each other, and there are at least 10 carbon atoms in the combined chain lengths of the hydrophobic linkers.

20. The zwitterionic ligand as claimed in claim 19, wherein the zwitterionic ligand has a formula II:

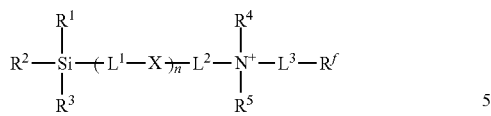

wherein $R^1$, $R^2$, $R^3$ are independently selected from a hydroxyl group, a halogen atom, an alkoxy group, a dialkylamino group, an acyl group, an alkyl group, or an aryl group;

$L^1$, $L^2$ and $L^3$ are independently hydrophobic moieties; each containing 2 to 30 carbon atoms, wherein there are at least 10 carbon atoms in the combined chain lengths of $L^1$, $L^2$ and $L^3$;

X is an O atom, S atom, amide group or sulfonamide group;

n is 0 or 1;

$R^4$, $R^5$ are independently selected from a hydrogen atom or a hydrocarbon moiety containing 1 to 20 carbon atoms; and $R_f$ is a negatively charged moiety selected from the group consisting of a sulfonic, a carboxylic, and a phosphonic functional group.

\* \* \* \* \*